United States Patent
Wang et al.

(10) Patent No.: US 8,658,013 B2
(45) Date of Patent: Feb. 25, 2014

(54) SENSOR AND SENSING METHOD

(75) Inventors: Da Yu Wang, Troy, MI (US); Walter Thomas Symons, Grand Blanc, MI (US); Robert Jerome Farhat, Grosse PTE Park, MI (US); John E. Kirwan, Troy, MI (US); Joachim Kupe, Davisburg, MI (US); Kenneth D. Mowery, Noblesville, IN (US)

(73) Assignee: Delphi Technologies, Inc., Troy, MI (US)

( * ) Notice: Subject to any disclaimer, the term of this patent is extended or adjusted under 35 U.S.C. 154(b) by 1722 days.

(21) Appl. No.: 11/292,179

(22) Filed: Dec. 1, 2005

(65) Prior Publication Data

US 2007/0125647 A1   Jun. 7, 2007

(51) Int. Cl.
*G01N 27/409* (2006.01)
*G01N 27/41* (2006.01)

(52) U.S. Cl.
USPC ............................ 204/424; 204/431; 205/782

(58) Field of Classification Search
USPC .......... 204/400, 401, 421–435; 205/781–785; 73/23.31, 23.32
See application file for complete search history.

(56) References Cited

U.S. PATENT DOCUMENTS

| | | | |
|---|---|---|---|
| 4,284,487 A * | 8/1981 | Barnes et al. | 204/408 |
| 4,547,281 A * | 10/1985 | Wang et al. | 204/424 |
| 5,433,830 A * | 7/1995 | Kawai et al. | 205/783.5 |
| 5,755,941 A * | 5/1998 | Weyl | 204/424 |
| 6,136,170 A * | 10/2000 | Inoue et al. | 204/424 |
| 6,471,840 B1 | 10/2002 | Gao et al. | |
| 6,638,416 B2 * | 10/2003 | Wang et al. | 205/775 |
| 6,673,223 B2 * | 1/2004 | Kunimoto et al. | 204/426 |
| 2002/0022163 A1 * | 2/2002 | Breuer et al. | 429/19 |
| 2002/0108855 A1 * | 8/2002 | Wang et al. | 204/425 |

(Continued)

FOREIGN PATENT DOCUMENTS

| | | |
|---|---|---|
| DE | 37 33 192 | 10/1988 |
| EP | 0 259 093 | 3/1988 |

(Continued)

OTHER PUBLICATIONS

Reigel, J., et al.: "Exhaust gas sensors for automotive emission control"; Solid State Ionics, North Holland Pub. Company, Amsterdam, NL, vol. 152-153, Dec. 2002, ISN: 0167-2738.
European Search Report dated Aug. 29, 2007.

*Primary Examiner* — Luan Van
*Assistant Examiner* — Gurpreet Kaur
(74) *Attorney, Agent, or Firm* — Mark H. Svoboda

(57) ABSTRACT

A sensor includes an oxygen pump cell; an oxygen pump chamber; an emf cell; a reference chamber providing a fluid connection to the reference gas; gas channels in fluid communication with the pump and emf electrodes, the reference gas comprising reformate produced by a fuel reformer fueled by an air-fuel gas mixture having an air-fuel ratio; a reformer electronic control module; a sensor electronic control module; a heater; a temperature sensor disposed in communication with the heater and the sensor control module for maintaining the sensor at a desired operating temperature; a closed loop controlled operation amplifier in electrical communication with the sensor, whereby the oxygen pump cell provides sufficient oxygen ions to oxidize an incoming diffusion-limiting fuel flux to the emf cell and maintain a constant emf at the emf cell, and wherein a current value represents an equivalent to the air-fuel ratio of the air-fuel gas mixture.

16 Claims, 18 Drawing Sheets

(56) References Cited

U.S. PATENT DOCUMENTS

| | | | |
|---|---|---|---|
| 2002/0110713 A1 | 8/2002 | Reindl et al. | |
| 2002/0187890 A1* | 12/2002 | Naka et al. | 502/38 |
| 2003/0057109 A1 | 3/2003 | Wang et al. | |
| 2003/0057968 A1 | 3/2003 | Wang et al. | |
| 2004/0202227 A1* | 10/2004 | Nelson et al. | 374/208 |
| 2006/0151338 A1* | 7/2006 | Wang et al. | 205/780.5 |

FOREIGN PATENT DOCUMENTS

| | | |
|---|---|---|
| WO | 99/26051 | 5/1999 |
| WO | 02/42756 | 5/2002 |
| WO | 2004/064184 | 7/2004 |

\* cited by examiner

SENSOR AND SENSING METHOD

TECHNICAL FIELD

The present disclosure relates to sensors and more particularly relates to oxygen to carbon ratio sensors and a method for forming same.

BACKGROUND

Significant research effort is currently underway to develop fuel reformer technology and applications. A fuel reformer mixes liquid fuels with a controlled quantity of air and cracks the fuel into a mixture of gases generally comprising hydrogen ($H_2$), carbon monoxide (CO), and small amounts of carbon dioxide ($CO_2$), water ($H_2O$), and methane ($CH_4$). This mixture of gases is termed "reformate." Reformate provides a clean fuel that can be used in other energy conversion devices such as internal combustion engines or fuel cells such as solid oxide fuel cells. Reference, for example, U.S. Pat. Nos. 6,230,494, 6,655,325, 6,609,582, and 6,485,852, the disclosures of each of which are totally incorporated by reference herein. Alternatively, reformate can be used as an improvised source of reducing gas for other pollutant treatment systems such as, for example, nitrogen oxides (NOx) absorber regeneration systems. A fuel reformer, together with a water shift reactor, can further enrich $H_2$ concentration by converting CO and $H_2O$ into $H_2$ and $CO_2$. Such a system is the source of hydrogen fuel for hydrogen burning engines or proton exchange member (PEM) fuel cells.

It is desirable to control the oxygen to carbon (O/C) ratio of the air-fuel (A/F) mixtures supplied to the reformer. Ideally, one would like to maintain an O/C ratio of unity, providing just enough oxygen to crack hydrocarbon liquid fuel in $H_2$ and CO with minimum production of $CO_2$ and $H_2O$. However, a stoichiometric supply of oxygen would, inadvertently, raise the reformer temperature to a point where the reformer catalyst can be thermally damaged, for example, above about 1000° C. for precious metal or non-precious metal type catalysts. An inadequate O/C ratio together with low temperature, for example, temperature in the range of below about 800° C. to about 550° C., can form carbons also, which can poison the reformer catalyst as well as poison down stream fuel cell electrodes in those systems wherein the reformer is providing fuel stock to a fuel cell. Further, the release of soot can pollute the environment.

In bench testing, it has been shown that it is possible to monitor reformate O/C ratio using a mass spectrometer. However, such an approach is not practical for real world applications.

Sensors, for example A/F ratio sensors, are known. Exhaust gas sensors are used in a variety of applications that require qualitative and quantitative analysis of gases. For example, exhaust sensors have been used for many years in automobiles to sense the presence of selected exhaust gases. Traditional A/F ratio sensors use air or oxygen as a reference gas. In automotive applications, the direct relationship between various exhaust gas concentrations and the air-to-fuel ratios of the fuel mixture supplied to the engine allows the sensor or sensors to provide concentration measurements for determination of optimum combustion conditions, maximization of fuel economy, and management of exhaust emissions. Reference, for example, U.S. Pat. Nos. 5,369,956, 6,295,809, 6,532,736, 6,579,435, 6,616,820, 6,746,584, 6,797,138, the disclosures of each of which are totally incorporated by reference herein.

Most sensors have outputs that are functions of temperature. The sensor output will vary as sensor temperature varies. To solve this problem, the sensor can be operated at a constant temperature, or the sensor is operated at a variable temperature which is measured in order to correct for the effect of temperature variation on sensor signal outputs. In either case, a temperature sensor and typically a heater, is built in to the sensing device.

When accurate measurement of the primary sensor is required, the precision of temperature (or associated controls) can present a challenge, particularly, for example, in exhaust gas species sensing applications. As air quality legislation in both Europe and North America become tighter and tighter, current sensor performance must be adjusted to meet the demands. Requirements include precision along with high temperature durability and poison resistance.

Exhaust sensors using zirconia electrolyte impedance as the temperature indicator are known. Zirconia impedance is exponentially dependant on temperature, becoming smaller at higher temperature, which makes it unsuitable for high temperature sensing. Further, the high non-linearity of zirconia at higher temperatures adds complexity to the control algorithm.

Resistance Temperature Detector (RTD) technology is disclosed, for example, in Published U.S. patent application Ser. No. 10/004,679 (Document Number 20030101573A1) assigned to the present Assignee, the disclosure of which is totally incorporated by reference herein. Linear RTD type temperature sensors have been incorporated with other sensing devices. Linear RTD sensors-use a thick film, multi-layer architecture. Typically, the RTD is screen printed using gold (Au) lines because with gold it is possible to achieve a high resistance value in a small area. Due to the low melting points of gold or gold alloys, this approach is not suitable for high temperature exhaust applications. Platinum (Pt) can sustain high temperatures such as experienced in combustion exhaust applications. However, the high conductivity of platinum renders screen printing fabrication approach difficult as it is difficult to achieve a high resistance value in a small area as required by RTD applications.

The disclosures of each of the foregoing U.S. patents are each totally incorporated herein by reference in their entireties. The appropriate components and process aspects of the each of the foregoing U.S. patents may be selected for the present disclosure in embodiments thereof.

What is needed is a practical, cost effective, and easy to manufacture device and method for monitoring and controlling the O/C ratio of an air fuel mixture feeding a fuel reformer.

SUMMARY

Provided are sensors, for example, reformate species sensors, for determining an oxygen to carbon (O/C) ratio in reformate (or exhaust) that can be applied, for example, to gasoline reformers, diesel reformers, methane reformers, methanol reformers, or a combination thereof, for on board diagnosis or for O/C ratio control. Also provided is a sensor comprising a reformate species sensor for determining a hydrogen to carbon ratio of the reformate for determining a quality of the fuel feeding the reformer. The sensing principle is based on electrochemical ampere-metric principles. Further provided is a method to fabricate the sensor using thick film multi-layer technology. The sensing element includes for example a pump cell, an emf (electromagnetic force) cell, and a heater, for a zirconia pump cell, a zirconia emf cell, and an alumina-platinum heater. Also provided is a sensing method comprising for example a sensor for measuring the gas fuel vapor concentrations of an exhaust, such as a reformer gas (reformate) species concentrations, and determining the O/C ratio based on the correlation between the O/C ratio and the rich fuel vapor concentration. The O/C ratio sensor and method tracks the changes in O/C ratios well, as illustrated by gas bench testing operated with simulated gas mixtures having compositions based on real analyses of reformate produced by a reformer operated at different O/C ratios. When tested in a reformer, the steady and transient results indicated an O/C sensor tracking between the O/C ratios of 1.03 and 1.09 with an observed signal noise of 1.6%. With this noise level, an O/C ratio resolution of about 0.01 is obtained without signal averaging. With signal averaging, the O/C ratio resolution is improved, for example to about 0.05. Considering a sensor output peak at the unit O/C ratio stoichiometric point, the peak position and signal strength is used, in embodiments, to calibrate the effect of fuel quality (that is, H/C ratio) and reformer aging on the O/C ratio resolution of the sensor.

Aspects illustrated herein relate to a sensor comprising an oxygen pump cell having a first pump electrode and a second pump electrode disposed on opposite sides of a first solid electrolyte layer; the first pump electrode being directly exposed to a reference gas or indirectly exposed to the reference gas through a protective coating layer and the second pump electrode being exposed to an oxygen pump chamber including a first aperture providing a fluid connection to the reference gas; an emf cell having a first emf electrode and a second emf electrode disposed on opposite sides of a second solid electrolyte layer; the first emf electrode sharing the same oxygen pump chamber as the second pump electrode and the second emf electrode being exposed to a reference chamber having a second aperture providing a fluid connection between the second emf electrode and the reference gas; wherein the reference gas comprises reformate produced by a fuel reformer fueled by an air-fuel gas mixture having an air-fuel ratio and including a reformer electronic control module; a sensor electronic control module in communication with the sensor and further in communication with the reformer electronic control module; a heater disposed in thermal communication with the sensor; a temperature sensor disposed in communication with the heater and in electronic communication with the sensor control module for maintaining the sensor at a desired operating temperature; and a closed loop controlled operation amplifier in electrical communication with the sensor, whereby the oxygen pump cell provides sufficient oxygen ions to oxidize an incoming diffusion-limiting fuel flux to the emf cell and maintain a constant emf at the emf cell, and wherein a current value represents an equivalent to the air-fuel ratio of the air-fuel gas mixture.

Further aspects illustrated herein relate to a method for forming a sensor comprising forming an oxygen pump cell by disposing a first pump electrode on a first exterior side of a first solid electrolyte layer and disposing a second pump electrode on a second opposite side of the first solid electrolyte layer; the first pump electrode being directly exposed to the reference gas or indirectly exposed to the reference gas through a protective coating layer and the second pump electrode being exposed to an oxygen pump chamber including a first aperture providing a fluid connection to the reference gas; forming an emf cell by disposing a first emf electrode on a first side of a second solid electrolyte layer and a second emf electrode on a second opposite side of the second solid electrolyte layer; forming a reference gas chamber including a second aperture providing a fluid connection to the reformate reference gas and to the second emf electrode; the first emf electrode sharing the same oxygen pump chamber as the second pump electrode and the second emf electrode being exposed to a reference chamber having a second aperture providing a fluid connection between the second emf electrode and the reference gas; disposing a heater in thermal communication with the sensor; disposing a temperature sensor in communication with the heater, to form a green sensor; firing or co-firing the green sensor; providing a fuel reformer for producing the reference gas, the fuel reformer being fueled by an air-fuel gas mixture having an air-fuel ratio; providing a reformer electronic control module in electrical communication with the reformer; providing a sensor electronic control module in electrical communication with the sensor, the reformer electronic control module, and the temperature sensor; and providing a closed loop controlled operation amplifier in electrical communication with the sensor, whereby the oxygen pump cell provides sufficient oxygen ions to oxidize an incoming diffusion-limiting fuel flux to the emf cell and maintain a constant emf at the emf cell, and wherein a current value represents an equivalent to the air-fuel ratio of the air-fuel gas mixture.

Further aspects illustrated herein relate to a sensing method comprising using the sensor disclosed herein for a sensing method comprising measuring reformate species concentrations; and determining an oxygen to carbon ratio based on a correlation between the oxygen to carbon ratio and a rich fuel vapor concentration.

Aspects herein provide a sensing element comprising a sensor; a heater; a resistance temperature detector sensor comprising an insulating layer having a high temperature ॥ resistance element disposed thereon; and a glass layer disposed between the resistance temperature detector sensor and the heater.

As used herein, high temperature means, for example, a temperature of about 800° C. to about 1000° C. The present high temperature capable RTD (Resistance Temperature Detector) sensor includes, for example, a sensing element sensor having a substrate, for example a ceramic substrate, including a plurality of leads, for example, about 6 to about 8 leads a built-in platinum heater (using up to about two leads), and an area allowing the attachment of a high temperature RTD sensor (using, for example, up to about two additional leads). The substrate serves as a protective coating layer protecting the RTD from poisoning, such as soot contamination. Additional leads, for example about two to about four leads, can be used for the primary sensing functions. The RTD sensor is suitable for use with various sensing elements, particularly high temperature applications of about 800° C. to about 1000° C. such as are encountered in combustion exhaust gas sensing applications, including, but not limited to, oxygen sensors such as wide range oxygen sensors, ammonia sensors, and the like. The RTD sensors can be fabricated together with the substrate at the same time.

Provided is a practical, cost effective, and easy to manufacture device and method suitable for example for monitoring and controlling an O/C ratio in an air fuel mixture used to feed a fuel reformer. Further provided is a sensor that can monitor an O/C ratio in reformate produced by a fuel reformer. The sensor senses the O/C ratio of reformate and further provides a device and method for detecting the quality of the fuels and aging level of the reformer catalyst. For example, a catalyst aging level sensor for sensing an aging level of a reformer catalyst provides in conjunction with a sensor control module and a reformer control module a measuring device for measuring a change in maximum peak strength of a sensor output and a calibration device for calibrating a catalyst aging effect on the oxygen to carbon ratio determination.

These and other features and advantages of the invention will be more fully understood from the following description of certain specific embodiments of the invention taken together with the accompanying drawings wherein like elements are numbered alike in the figures.

DESCRIPTION

Figure 1:
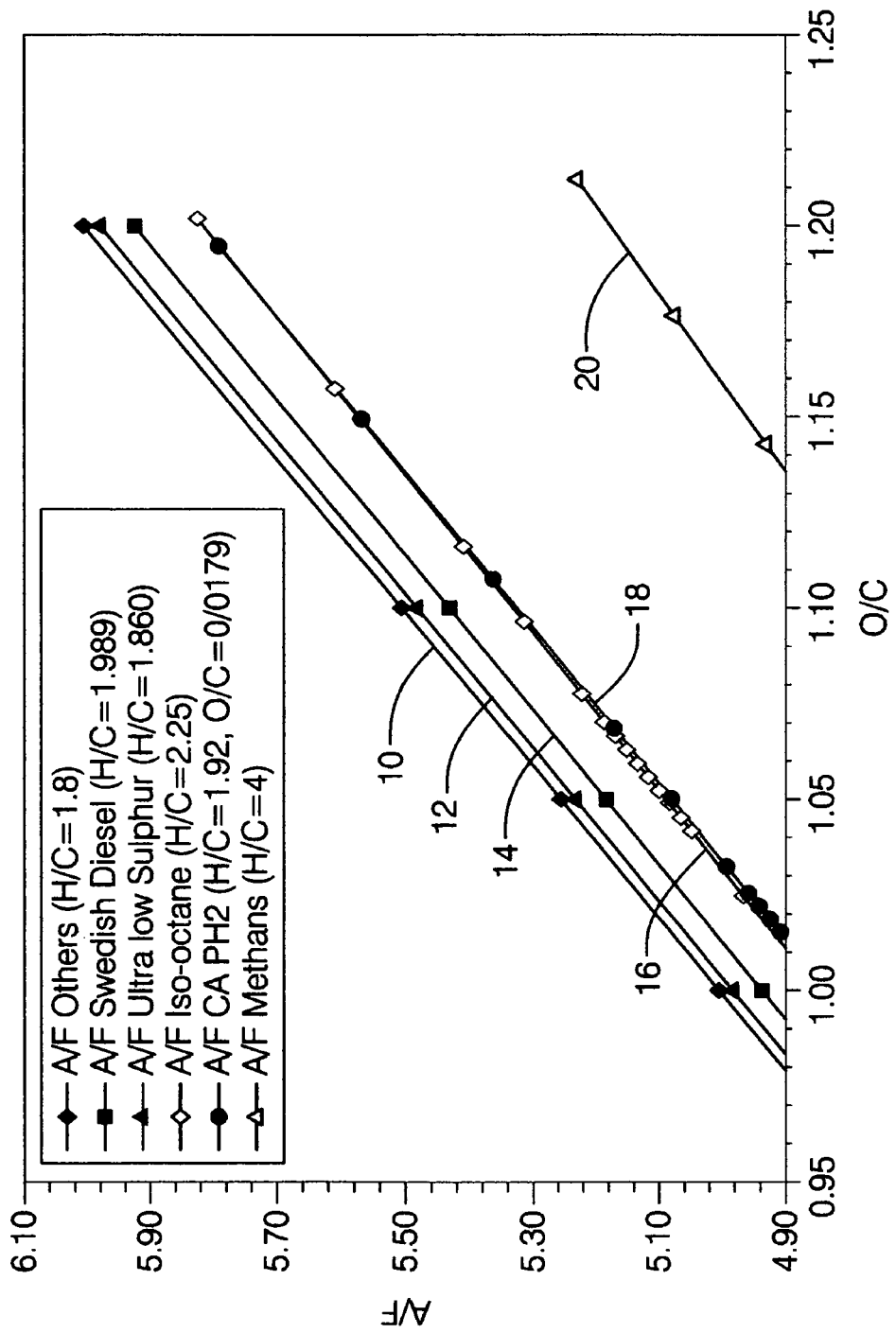
FIG. 1 is a graph illustrating air fuel ratio (y-axis) versus oxygen to carbon ratio (x-axis) for various grades of diesel fuels.

An oxygen to carbon (O/C) ratio sensor provides a cost effective and easily manufactured device and method for monitoring O/C ratio, for example in reformats. The O/C sensing principle is based on the fact that there is a correlation between the air to fuel (A/F) ratio and the O/C ratio for diesel and gasoline fuels. Referring to FIG. 1, the A/F ratio (y-axis) versus O/C ratio (x-axis) for various grades of diesel fuels having various hydrogen to carbon (H/C) ratios in the range of about 1.8 to about 2.0, with line 10 illustrating an A/F versus O/C ratio for a diesel fuel having a H/C of about 1.8, line 12 illustrating an A/F versus O/C ratio for an ultra low sulfur diesel fuel having a H/C of about 1.860, line 14 illustrating an A/F versus O/C ratio for a Swedish diesel fuel having a H/C of about 1.989, line 16 illustrating an A/F versus O/C ratio for an isooctane diesel fuel having a H/C of about 2.25, line 18 illustrating an A/F versus O/C ratio for a CA PH2 (California Phase 2 Fuel) diesel fuel having a H/C of about 1.92 and an O/C of about 0/0179, and line 20 illustrating an A/F versus O/C ratio for a methane fuel having a H/C of about 4. As shown in FIG. 1, there is a linear correlation between the A/F ratio and the O/C ratio with an O/C uncertainty of about ±0.010. The gain factor between $\Delta(H/C)$ and $\Delta(O/C)$ is estimated to be about 10:1. Therefore, knowing the A/F ratio, the O/C ratio can be determined, as long as the fuel does not have a large variation in its H/C ratio, that is, a variation that is larger than about +0.1 to about −0.1. This resolution limit can be totally eliminated if the quality of the fuel (H/C ratio) is known.

A/F ratio sensing technology has long been developed for automobile engine A/F ratio control applications. Reference, for example, U.S. Pat. Nos. 6,746,584, 6,723,217, 6,572,747, 6,497,135, 6,482,310, and 6,481,273, the disclosures of each of which are totally incorporated by reference herein in their entireties. The sensor is based on electrochemical amperemetric principle. Typically, it is composes an electrochemical emf cell and an oxygen pump cell. Using a closed loop controlled operation amplifier, the pump cell would provide adequate oxygen ions (current) to oxidize the incoming diffusion-limiting fuel flux to the emf cell and maintain a constant emf at the emf cell. The current represents the equivalent of A/F ratio of the gas mixture.

An O/C sensor is provided using reformate as the reference gas for its emf cell. The structure provides the advantages of ease of operation and elimination of air-leak related safety concerns. The sensor architecture is based on multi-layer thick film technology and provides a cost effective and easy to manufacture device.

Figure 2:
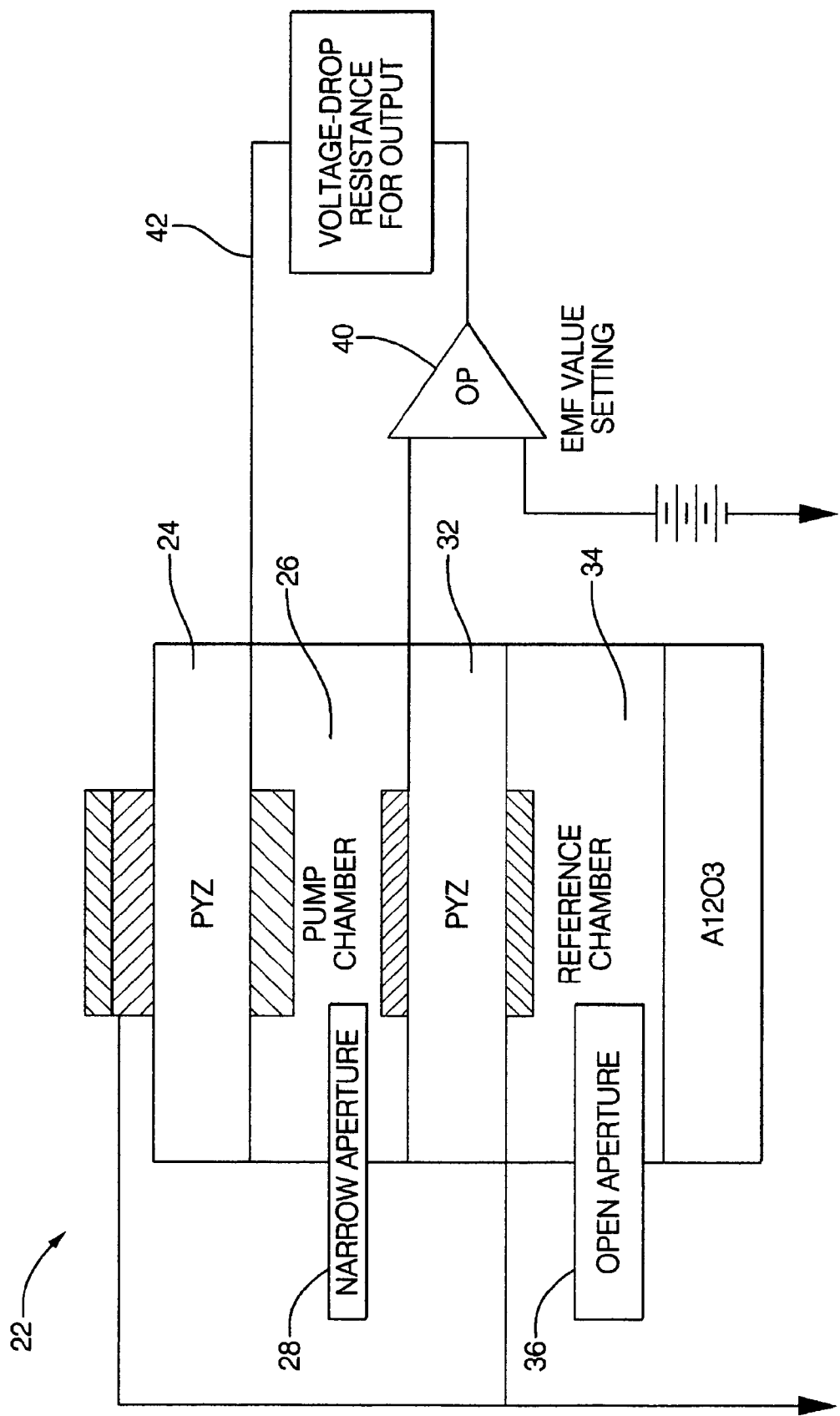
FIG. 2 is a diagram of an O/C sensor.

The O/C ratio sensor measures the limiting oxygen current electrochemically. For example, a method is disclosed comprising measuring a limiting oxygen current electrochemically, using the measured limiting oxygen current to balance fuel flux diffused into the oxygen pump chamber; and balancing a fuel flux using a gas diffusion limiting porous aperture provided to the pump chamber. As illustrated in FIG. 2 (further described herein below), the oxygen current is used to balance the fuel flux diffused into the emf cell. A porous controlled aperture of the emf cell provides the gas diffusion limiting means to limit the fuel flux. Fick's first law describes the limiting fuel flux or the oxygen current I as $$I = -(ncFDA)(\partial x/\partial y) + 1x \quad (1)$$

with the solution as, $$I = (ncFDA/L)\log_e(1-x_{in}/1-x) \quad (2)$$

in which c is the molar concentration of fuel vapor,
F is the Faraday constant,
D is the gas diffusion constant,
A is the effective diffusion cross section of the gas diffusion limiting aperture,
L is the effective diffusion length of the gas diffusion limiting aperture,
X is the concentration of the fuel gas,
$X_{in}$ is the concentration of the fuel gas inside the chamber formed between the pump cell and the emf cell, and N is the number of charges involved in the reaction.

For example, for $H_2$, n=2, for CO, n=2, for $CH_4$, n=8, for $O_2$, n=4.

When x is small, the solution becomes linear, $$I = -(ncFDA/L)(x_0 - x) \quad (3)$$

Based on gas molecular diffusion model, the diffusion constant in Equations 1, 2, and 3, for a bi-gas system, can be described as $$D_M \propto T^{1.75} P^{-1} (V_A^{1/3} + V_B^{1/3})^{-2} (1/M_A - 1/M_B)^{0.5} \quad (4)$$

In which $D_M$ is the gas molecular diffusion constant,
T is temperature of the gas,
P is pressure of the gas,
$V_A$ is the molecular gas diffusion volume of the first gas is the b-gas system,
$V_B$ is the molecular gas diffusion volume of the second gas in the bi-gas system,
$M_A$ is the molecular weight of the first gas is the b-gas system,
$M_B$ is the molecular weight of the second gas in the bi-gas system, In the case the that the mean free path of the gas molecule is larger than the pore sizes of the aperture (that is, the Knudsen diffusion mechanism), there is no bulk flow contribution (the last term in Equation 1) and the solution is the same as Equation 3, except the diffusion constant is defined by the Knudsen diffusion mechanism which is $$D_K \propto (T/M_g)^{0.5} \quad (5)$$

Wherein $D_K$ is Knudsen diffusion constant,
T is absolute temperature of the gas, and
$M_g$ is molecular weight of the gas.

Using Equations 4 and 5, the diffusion constant value can be estimated and the limiting current ratios between different gas systems can be calculated. The results of limiting current ratios for various bi-gas systems are shown in Table 1.

TABLE 1

| n | $CH_4$—$N_2$ 8 | $H_2$—$N_2$ 2 | CO—$N_2$ 2 | $O_2$—$N_2$ 4 |
|---|---|---|---|---|
| $D_M/D_M(O_2)$ | 1.062 | 3.658 | 0.9891 | 1.000 |
| $D_K/D_K(O_2)$ | 1.060 | 3.984 | 1.069 | 1.000 |
| $I_M/I_M(O_2)$ | 2.123 | 1.829 | 0.4945 | 1.000 |
| $I_K/I_K(O_2)$ | 2.825 | 1.992 | 0.5344 | 1.000 | wherein n is the number of electrons exchanged for each fuel molecule in its oxidation half reaction,
$D_M/D_M(O_2)$ is the ratio of diffusion constant based on molecular diffusion (M),
$D_K/D_K(O_2)$ is the ratio of diffusion constant based on Knudsen diffusion mechanism (K),
$I_M/I_M(O_2)$ is the ratio of limiting current of the gas based on molecular diffusion model, and
$I_K/I_K(O_2)$ is the ratio of limiting current of the gas based on Knudson diffusion model. The ratios use an $O_2$—$N_2$ bi-gas system as the reference gas. As shown in Table 1, there is an almost equal contribution of different gas species to the limiting current, expect hydrogen. Therefore, the linear correlation between the A/F ratio and the O/C ratio shown in FIG. 1 will be observed only if the reformer has a steady and repeatable catalyst performance. If the reformer does not have a steady and repeatable catalyst performance, especially when the $H_2$ concentration of the reformate is not steady and repeatable, the sensor would provide different O/C ratio outputs even when the same air-fuel mixtures were delivered to the reformer.

Figure 18:
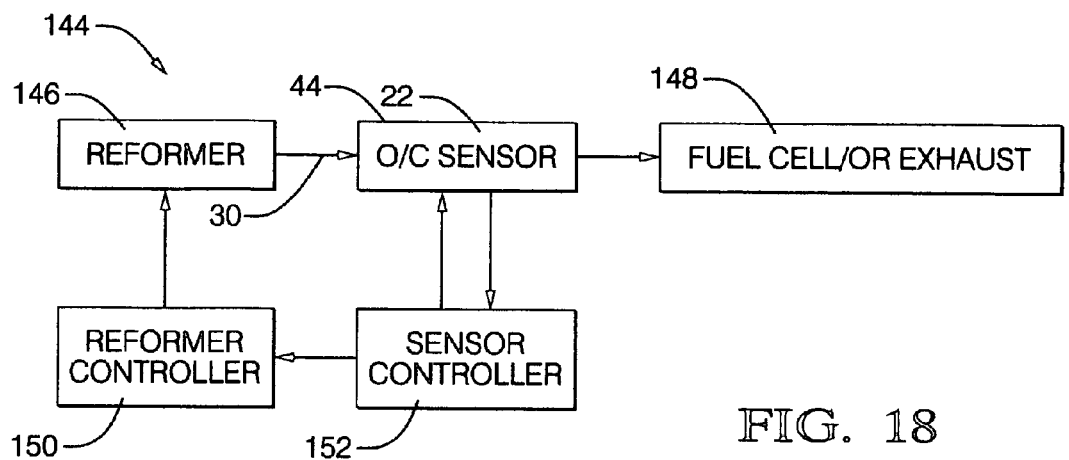
FIG. 18 is a schematic diagram of an O/C sensor employed in a reformer system.

Turning to FIG. 2, an O/C sensor 22 includes an oxygen pump electrochemical cell 24 having an oxygen pump chamber 26 including a first aperture 28, such as a narrow aperture 28 (for example, an aperture that is sufficiently narrow such that the limiting current in air can be obtained with, for example, a current limiting effect in air of between about, for example about 0 to about 1.5 volts (applied DC pump voltage) or an applied voltage of less than or equal to about 1.2 V pump voltage) providing a fluid connection to the reformate reference gas 30 (shown in FIG. 18). Emf electrochemical reference cell 32 includes a reference chamber 34 having a second aperture 36, such as an open aperture 36 (for example, with the open aperture there is no need to create a current limiting effect in air of between about, for example about 0 to about 1.5 applied DC pump voltage) for fluid connection to rich reformer gas 30, with aperture 36 connecting to the chamber 34. For example, the second aperture has an opening sufficient to maintain the second emf electrode at chemical equilibrium with the reference gas and having a high gas diffusion rate so that the response time of the second emf electrode is not limited by the response time of the gas diffusion rate of the second aperture. An operation amplifier 40 provides feed back loop control of the pump current 42 to keep the emf value of the emf cell 32 at a constant value.

Figure 3:
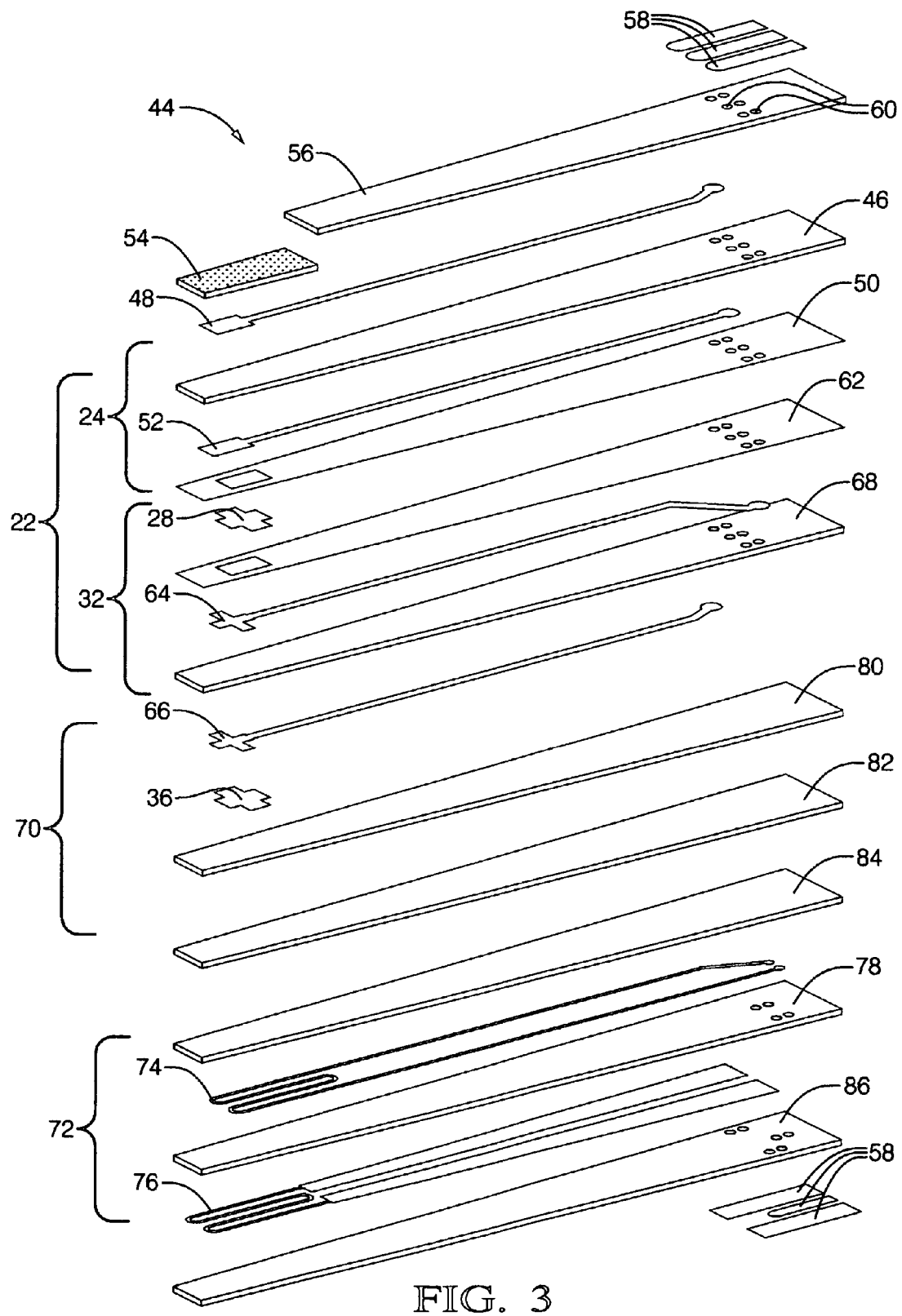
FIG. 3 is an exploded view of a sensing element including an O/C sensor.

Turning to FIG. 3, an exploded view showing the structural layout for a sensing element 44 including O/C sensor 22. In FIG. 3, sensing element 44 includes an oxygen pump cell 24 and an emf reformate gas reference cell 32. First pump electrode 48 is printed on a first side of solid electrolyte layer 46. Separating the solid electrolyte layer 46 from emf reformate gas reference cell 32 is an insulating (alumina) layer 50. Insulating layer 50 comprises an insulating material, for example, in embodiments, a dielectric material, such as, for example, alumina, cordierite, lanthanum oxide, strontium oxide, titania, strontium titanate, barium titanate, and the like, as well as combinations comprising at least one of the foregoing dielectric materials. A second pump electrode 52 is disposed on a second, opposite side of the solid electrolyte layer 46 and on the other side of the layer 46.

A protective coating layer 54 can optionally be disposed over the oxygen pump cell electrode 48 and an insulating layer 56 disposed over the oxygen pump cell 24. Electrical contact with electrode pad 58 is made by the lead portion of electrode 48 through vias 60 in insulating layer 56 so that the current signal can be detected from outside such as through amplifier 40 (shown in FIG. 2).

Another insulating layer 62 is disposed between the oxygen pump cell 24 and the emf reference cell 32. Insulating layer 62 enables fluid communication between the emf reference cell 32 and the exhaust gas. Emf reference cell 32 includes first emf electrode 64 and second emf electrode 66 disposed on opposite sides of electrolyte layer 68. Gas channel/aperture 36 is in fluid communication with the emf reference electrode 66. Aperture 36 enables fluid communications between the emf electrodes 64, 66, the pump electrode 52 gas and the reformer gas.

The emf electrodes 64 and 66 further comprise part of the temperature sensor 70.

Further disposed on a side of the emf reference cell 32 opposite the oxygen pump cell 24 is a heater such as heater 72 including electromagnetic shield 74 and heating element 76 disposed on opposite sides of dielectric layer 78. The heater is in communication with temperature sensor 70 for maintaining sensing element 44 at the desired operating temperature, for example, maintaining the sensor at a constant temperature during operation or maintaining the sensor at a variable temperature during operation. The heater can be for example any conventional heater capable of maintaining the sensor at a sufficient temperature to facilitate the various electrochemical reactions therein. The heater, which is typically platinum, alumina, palladium, and the like, as well as mixtures and alloys comprising at least one of the foregoing metals, or any other conventional heater, is generally screen printed onto a substrate to a thickness of about 5 microns to about 50 microns, although not limited.

Typically, one or more insulating layers such as insulating layers 80, 82, 84 and 86 are disposed between the emf reference cell 32 and the heater 72. Insulating layers and any support layers, are typically capable of providing structural integrity (for example, effectively protecting the gas sensor from abrasion, vibration, and the like, and providing physical strength to the sensor), and physically separating and electrically isolating various components. The insulating layer or layers, which can be formed using ceramic tape casting methods or other methods such as plasma spray deposition techniques, screen printing, stenciling and others conventionally used in the art, can each be up to about 200 microns thick, with a thickness of about 50 microns to about 200 microns preferred. In order to reduce the leakage current, high resistance dielectric materials can be employed, for example, materials, which at temperatures of about 800° C. have a current leakage of less than about 0.01 microamperes. Since the materials employed in the manufacture of gas sensors in specific embodiments comprise substantially similar coefficients of thermal expansion, shrinkage characteristics, and chemical compatibility in order to minimize, if not eliminate, delamination and other processing problems, the particular material, alloy or mixture chosen for the insulating layer can be selected based upon the specific electrolyte employed. For example, these insulating layers can comprise a dielectric material, such as alumina, cordierite, lanthanum oxide, strontium oxide, titania, strontium titanate, barium titanate, and the like, as well as combinations comprising at least one of the foregoing dielectric materials.

The electrolyte layers, such as layers 46 and 68, can comprise, for example, in embodiments a solid electrolyte that can comprise the entire layer or a portion thereof The electrolyte layer can be any material that is capable of permitting the electrochemical transfer of oxygen ions while inhibiting the physical passage of exhaust gases and is compatible with the environment in which the gas sensor will be utilized (for example, up to about 1,000° C.). Possible solid electrolyte materials can comprise any material conventionally employed as sensor electrolytes, including, but not limited to, zirconia which may optionally be stabilized (or doped) with calcium, barium, yttrium, magnesium, aluminum, lanthanum, cesium, gadolinium, and the like, as well as combinations comprising at lest one of the foregoing. For example, the electrolyte can be alumina and yttrium stabilized zirconia. Typically, the solid electrolyte, which can be formed via many conventional processes (e.g., die pressing, roll compaction, stenciling and screen printing, tape casting techniques, and the like), has a thickness of up to about 500 microns, particularly a thickness of approximately 25 microns to about 500 microns or about 50 microns to about 200 microns.

The electrolyte layers and protective layer or insulating layers can comprise the entire layer or any portion thereof For example, they can form the layer, be attached to the layer (protective material/electrolyte abutting a dielectric material), or disposed in an opening in the layer (protective material/electrolyte can be an insert in an opening in a dielectric material layer). The latter arrangement eliminates the use of excess electrolyte and protective material, and reduces the size of gas sensor by eliminating layers. Any shape can be used for the electrolyte and insulating layers, with the size and geometry of the various inserts, and therefore the corresponding openings, is dependent upon the desired size and geometry of the adjacent electrodes. It is preferred that the openings, inserts, and electrodes have a substantially similar geometry.

Furthermore, in additional to the protective layers, electrodes and leads thereto, heater, electrolyte layers and dielectric layers, additional conventional components can be employed in the sensing element, including but not limited to additional protective coatings (for example, spinel, alumina, magnesium aluminate, and the like, as well as combinations comprising at least one of the foregoing coatings, lead gettering layer(s), ground plane(s), support layer(s), additional electrochemical cell(s), and the like.

Electrodes such as oxygen pump cell electrodes 48, 52, emf reference electrode 64, 66 which are the temperature sensing electrodes, and any additional electrodes, etc. can comprise, but are not limited to, materials typically used in exhaust oxygen sensors such as metals including platinum, palladium, osmium, rhodium, iridium, gold and ruthenium; metal oxides such as zirconia, yttria, ceria, calcia, alumina and the like; other materials, such as silicon, and the like; and mixtures and alloys comprising at least one of the foregoing. As with the electrolyte layers, the electrodes can be formed using conventional techniques. Some possible techniques include sputtering, chemical vapor deposition, screen printing, and stenciling, among others. If a co-firing process is employed for the formation of the sensor, screen printing the electrodes onto appropriate tapes is preferred due to simplicity, economy, and compatibility with the co-fired process. For example, emf reference electrode can be screen printed onto an insulating layer or over a solid electrolyte layer.

Formation of the gas sensors described herein can be accomplished in any conventional fashion, for example, forming the individual layers of the sensor, firing the layers, and stacking the layers to form the sensor, or forming the green layers, stacking the layers, and co-firing to produce the sensor. For example, the protective layers, alumina layers, and solid electrolyte layers are formed using a doctor blade tape forming method. The desired vias are formed in these layers accordingly. Holes are also formed in the protective layers, alumina layers, and electrolyte layers using a punching technique.

Figure 4:
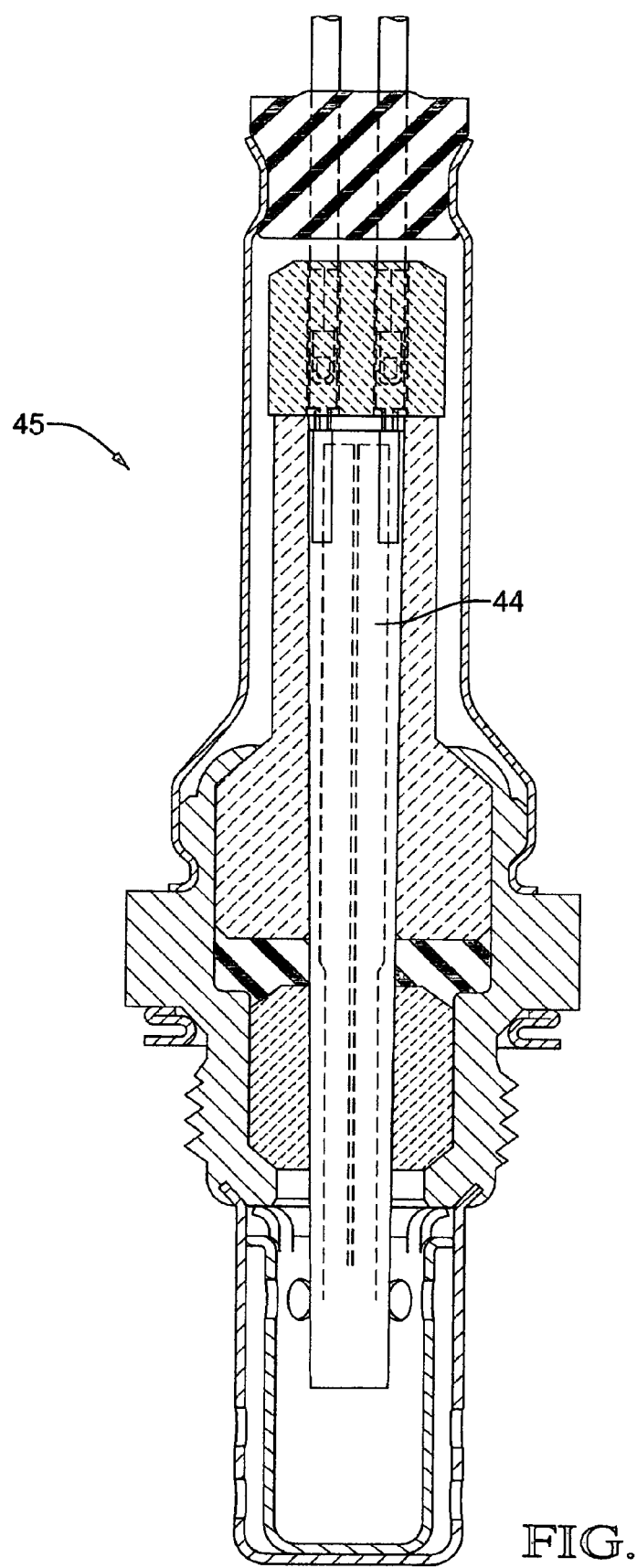
FIG. 4 is a cross-cut view of a packaged sensing element.

Thick film multi-layer sensor forming technology may be used to prepare the sensing elements. For example, alumina and yttria-alumina doped zirconia is made into a slurry and cast as standard thickness green tapes, i.e., about 200 microns thick. Heater, electrodes, electrode leads, and pads are printed onto the green tapes and the printed green tapes are thermally laminated, cut, and fired at about 1450° C. to about 1500° C. for about 2 hours. FIG. 4 shows a cross-cut view of a packaged sensor 45 including sensing element 44 shown inserted at the middle section of the packaged 45.

As noted above, the emf cell comprises, in embodiments, a solid electrolyte layer, for example an yttria doped zirconia layer, with two electrodes, such as platinum electrodes, disposed on opposite sides of the electrolyte layer. The devices are prepared, for example, by thick film multi-layer technology. For example, green tapes of yttria doped zirconia and alumina, for example, are cast from slurry. Electrodes and heaters are disposed on the tapes such as by screen printing. The printed tapes are thermally laminating and then fired, such as at a temperature of about 1450° C. to about 1500° C. for several hours.

In embodiments, the gas diffusion limiting aperture 28 comprises a porosity controlled material which is screen printed on the green ceramic tape with controlled dimensions. The type of porosity controlling material is selected with reference to the particular requirements. Exemplary porosity controlled materials include, but are not limited to, for example, carbon black, graphite, alumina-carbon-black, alumina-graphite, and combinations thereof.

The resistance of the electrolyte layer is used for temperature sensing. The heater is powered for example, by a constant voltage power supply.

Figure 5:
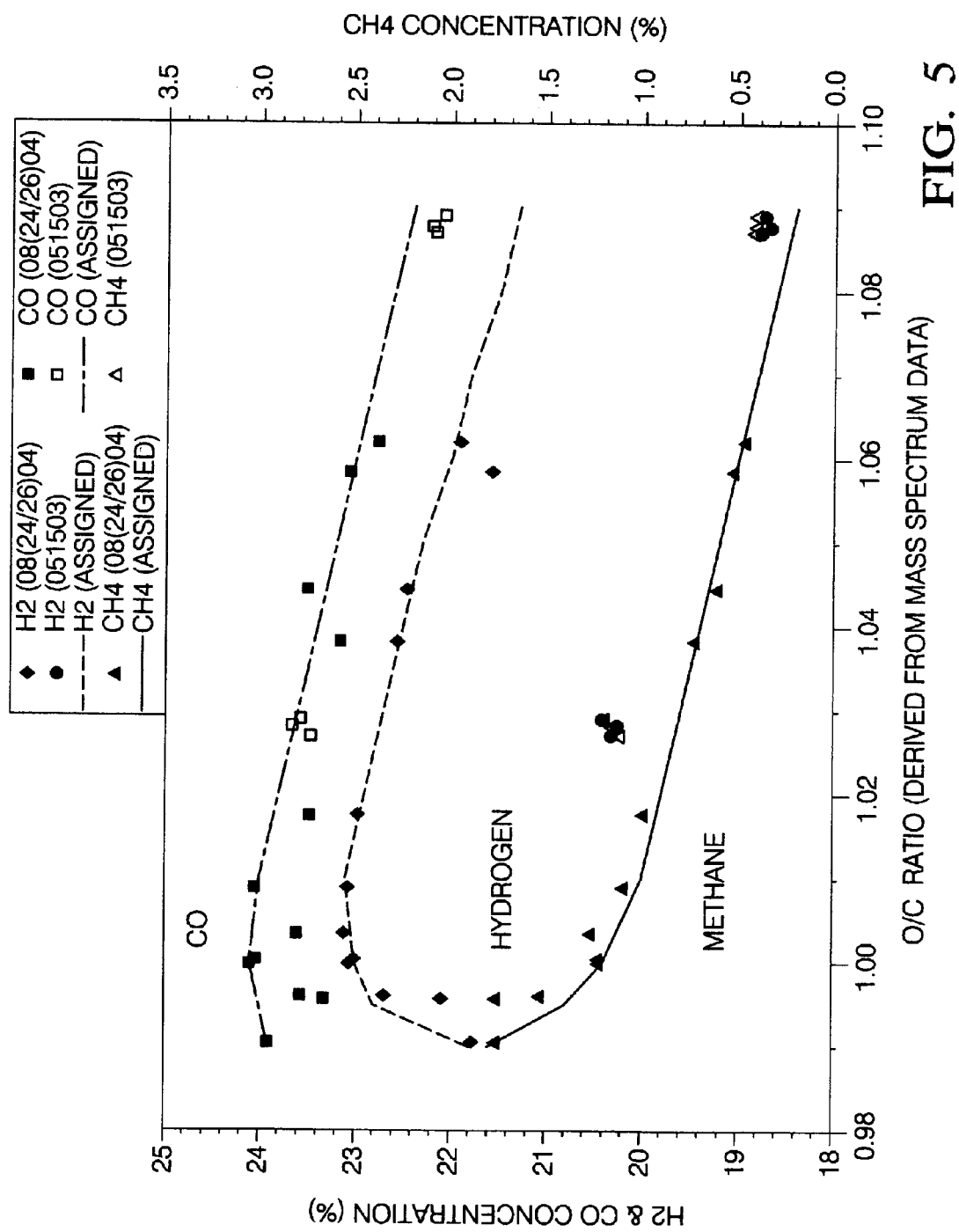
FIG. 5 is a graph illustrating CO, $H_2$ and $CH_4$ as a function of O/C ratio for a reformate gas produced by a reformer using diesel fuel.
Figure 6:
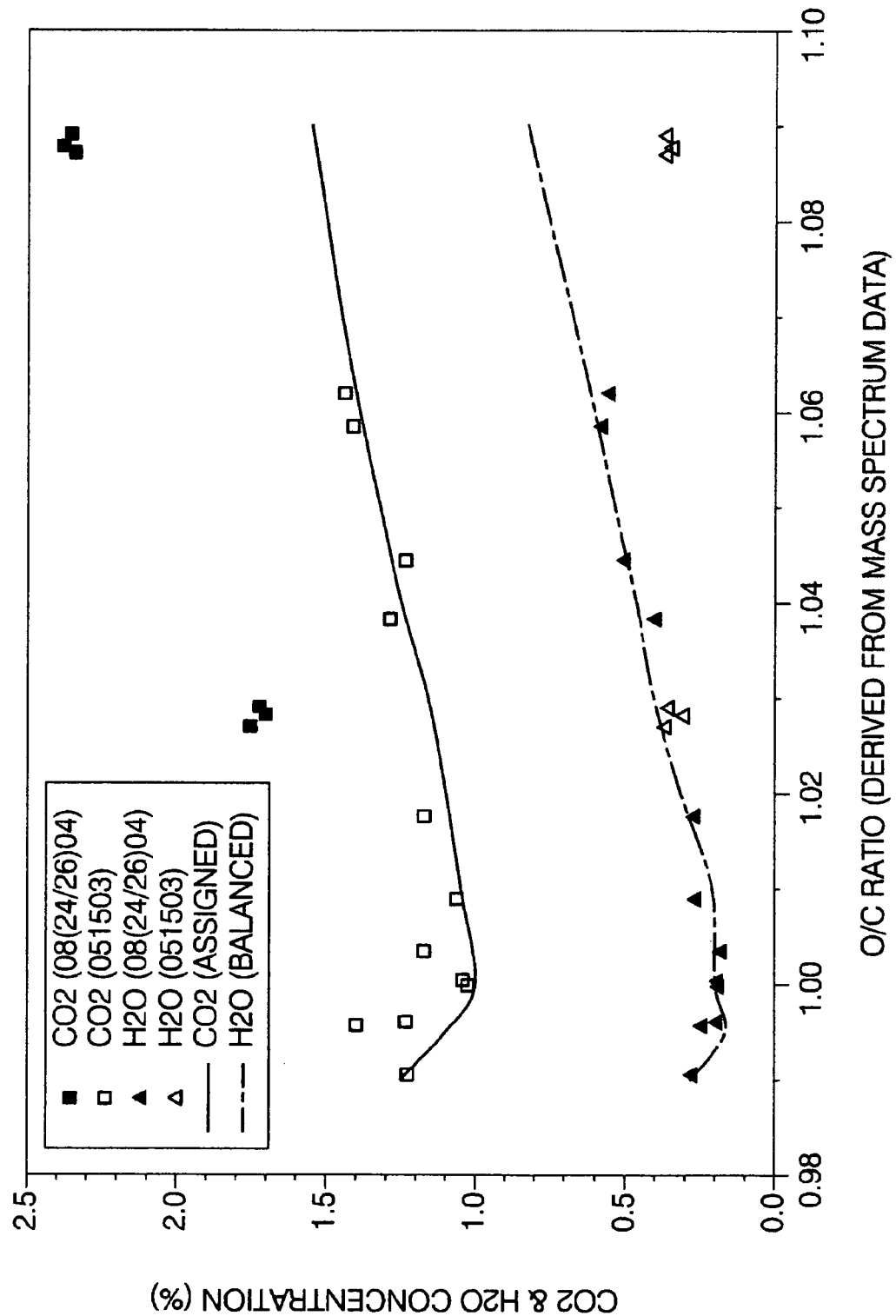
FIG. 6 is graph illustrating $CO_2$, and $H_2O$ as a function of O/C ratio for a reformate gas produced by a reformer using diesel fuel.

The gas compositions of reformate can be determined, for example by monitoring with a mass spectrometer. Based on the gas compositions, O/C ratio values can be calculated for the reformate gas. FIGS. 5 and 6 illustrate gas composition data that has been plotted against calculated O/C values for a reformer run with a diesel fuel having a H/C ratio close to 2. FIG. 5 shows a composition plot of CO, H2 and CH4 as the function of O/C ratio of a reformer using diesel as the fuel. FIG. 6 shows a composition plot of CO2, and H2O as the function of O/C ratio of a reformer using diesel as the fuel. The solid curves shown in FIGS. 5 and 6 represent the data shown in Table 2. Based on these figures, the gas composition as a function of O/C ratios is determined to vary between about 0.990 and about 1.090.

TABLE 2

Gas Composition of Reformer exhaust

| O/C | H2 (%) | CO (%) | CH4 (%) | CO2 (%) | H2O (%) | N2 (%) |
|---|---|---|---|---|---|---|
| 0.990 | 21.8 | 23.9 | 1.8 | 1.25 | 0.281 | 51.1 |
| 0.995 | 22.8 | 24.0 | 1.4 | 1.10 | 0.168 | 50.6 |
| 1.000 | 23.0 | 24.1 | 1.2 | 1.00 | 0.200 | 50.6 |
| 1.010 | 23.1 | 24.0 | 1 | 1.05 | 0.211 | 50.7 |
| 1.020 | 22.9 | 23.8 | 0.9 | 1.10 | 0.316 | 51.2 |
| 1.030 | 22.7 | 23.6 | 0.8 | 1.16 | 0.407 | 51.6 |
| 1.040 | 22.5 | 23.4 | 0.7 | 1.25 | 0.464 | 52.0 |
| 1.050 | 22.3 | 23.2 | 0.6 | 1.32 | 0.536 | 52.4 |
| 1.060 | 22.0 | 23.0 | 0.5 | 1.39 | 0.603 | 53.0 |
| 1.070 | 21.8 | 22.8 | 0.4 | 1.45 | 0.676 | 53.4 |
| 1.080 | 21.5 | 22.6 | 0.3 | 1.50 | 0.752 | 54.0 |
| 1.090 | 21.3 | 22.4 | 0.2 | 1.55 | 0.824 | 54.4 |

The following examples are set forth as representative of the present sensors and sensing method. These examples are not to be construed as limiting the scope of the disclosure as these and other equivalent embodiments will be apparent in view of the present disclosure and accompanying claims.

EXAMPLES

The sensing elements of Examples 1-4 were prepared using known thick film technology method as described herein generally comprising disposing an oxygen pump electrode comprising platinum particles and electrolyte particles and graphite or carbon black particles and an emf reference electrode comprising platinum particles and electrolyte particles and graphite or carbon black particles on opposite sides of an electrolyte layer; forming a reference gas channel in fluid communication with the reference electrode; disposing a heater in thermal communication with the sensor; disposing a temperature sensor in communication with the heater for maintaining the sensor at a desired operating temperature to form a green sensor. The green sensor was fired in an oven at a temperature of about 1450° C. for about 2 hours.

The O/C ratio sensors of Example 1, 2, and 3 were tested using a gas bench test comprising supplying gas mixtures from bottles of nitrogen, oxygen, carbon dioxide, carbon monoxide, hydrogen, and methane. The gas compositions were modulated by gas flow meters with the total gas flow rates being fixed at about 1 liter per minute. Periodically, the flow rates were increased to about 3 liters per mete to determine flow rate dependence. A room ambient temperature water bubbler to maintain the humidity of the gas at a constant level of about 1% of $H_2O$. The gas mixture was passed through a 3 foot tube that was heated inside an 800° C. furnace prior to introducing the mixture to the test sensors of Examples 1-3.

Figure 7:
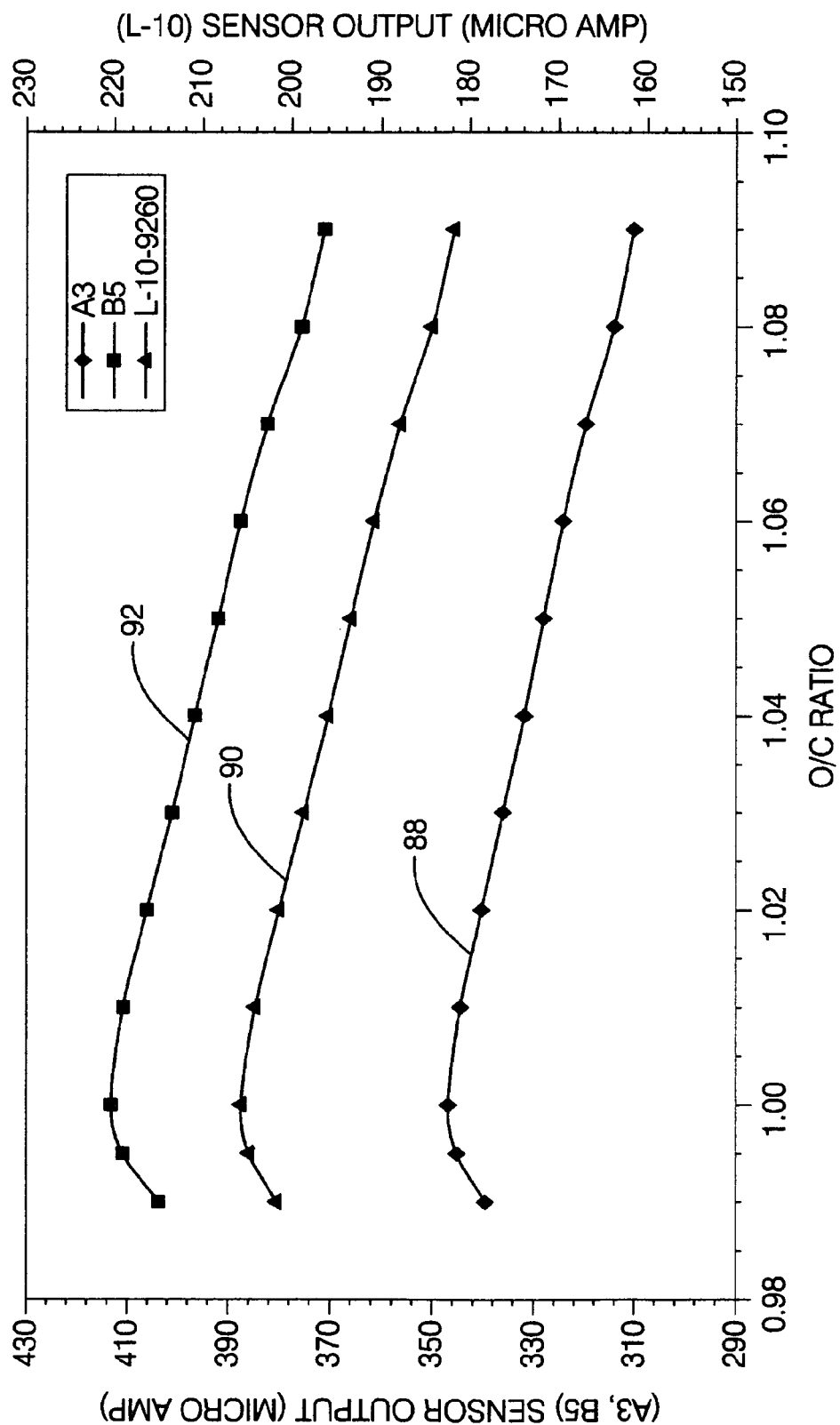
FIG. 7 is a graph illustrating limiting current outputs (y-axis) versus O/C ratios (x-axis) for three O/C sensors.

The O/C ratio sensors of Examples 1, 2 and 3 were tested on a gas bench with the gas compositions varied according to Table 2. The limiting current outputs of the Examples were plotted against the O/C ratios as shown in FIG. 7 illustrating sensor output in microamperes (y-axis) versus O/C ratio (x-axis) with line 88 referring to Example 1, line 90 referring to Example 2 and line 92 referring to Example 3. The three sensors were fully packaged as shown in FIG. 4 and were powered at 10.4 watt. Examples 1-3 showed different limiting current levels, but otherwise responded similarly as a function of O/C ratio peaking at the stoichiometric point of unity.

Figure 8:
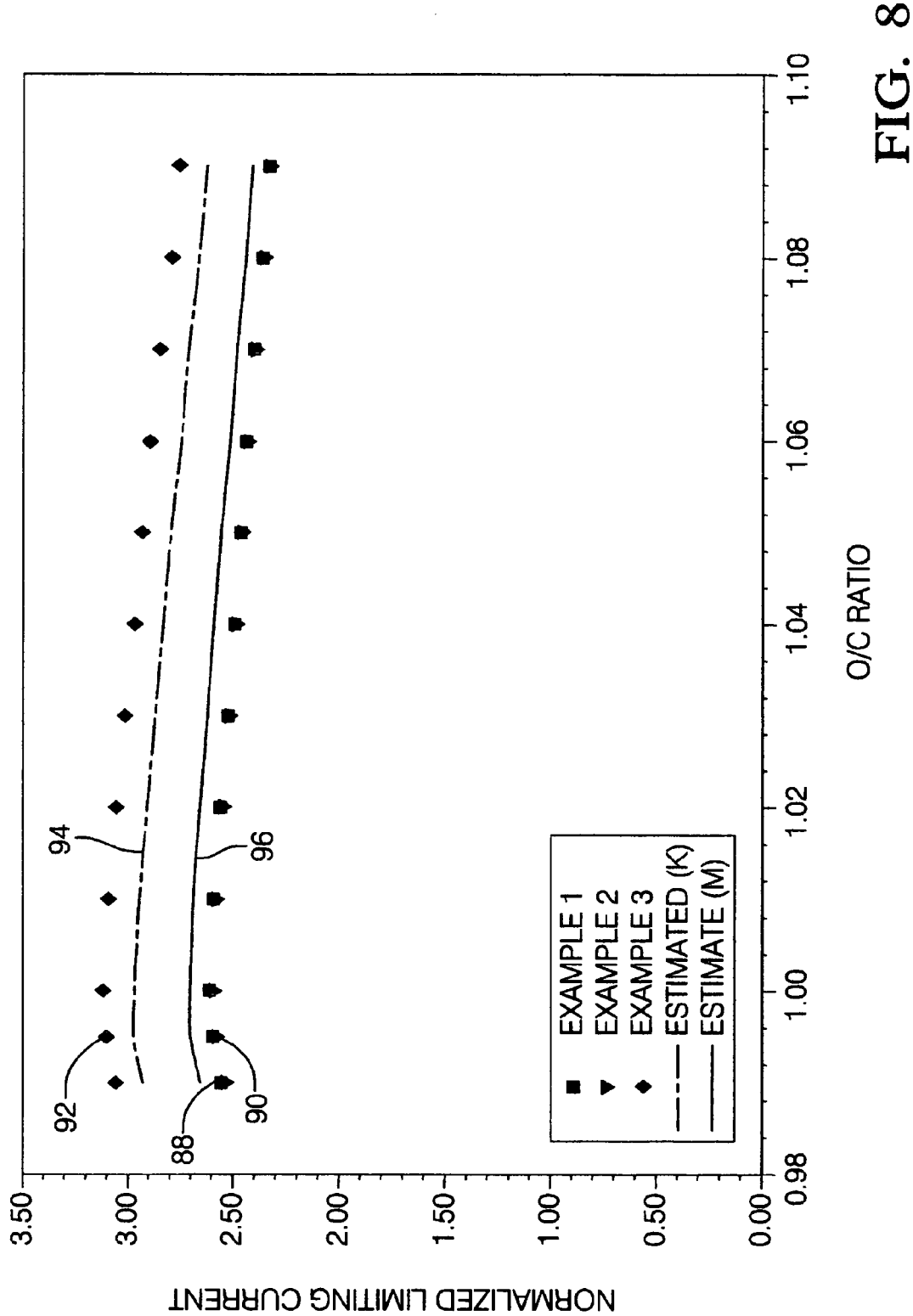
FIG. 8 is a graph illustrating normalized limiting current output (y-axis) versus O/C ratios (x-axis) for three O/C sensors.

The results shown in FIG. 7 were normalized with the air limiting current of the individual sensors of Examples 1-3 and the results are shown in FIG. 8 illustrating normalized limiting current (y-axis) versus O/C ratio (x-axis) with solid squares 92 referring to Example 1, solid triangles 90 referring to Example 2, and solid diamonds referring to Example 3. In FIG. 8, the upper dashed line 94 represents the model based on the Knudsen diffusion mechanism and the lower solid line 96 represents the model based on the gas molecular diffusion mechanism. As can be seen in FIG. 8, the sensors of Example 1 and Example 2 have an output that is closer to the molecular diffusion model with a discrepancy of about −4% and the sensor of Example 3 has an output that is closer to the Knudsen diffusion model with a discrepancy of about +6%.

Figure 9:
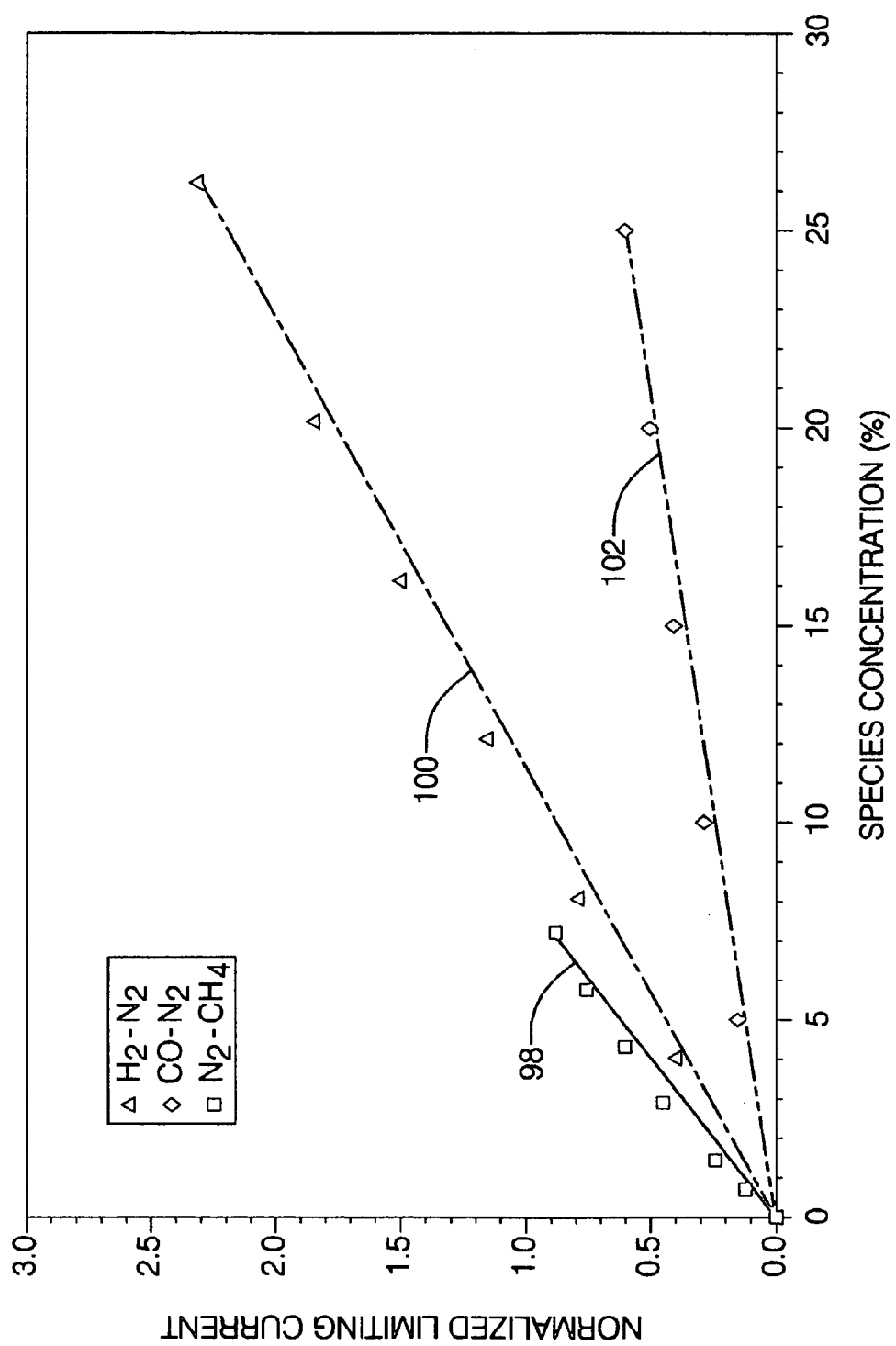
FIG. 9 is a graph illustrating normalized limiting current (y-axis) versus species concentration (x-axis) for an O/C sensor tested in three separate bi-gas systems.
Figure 10:
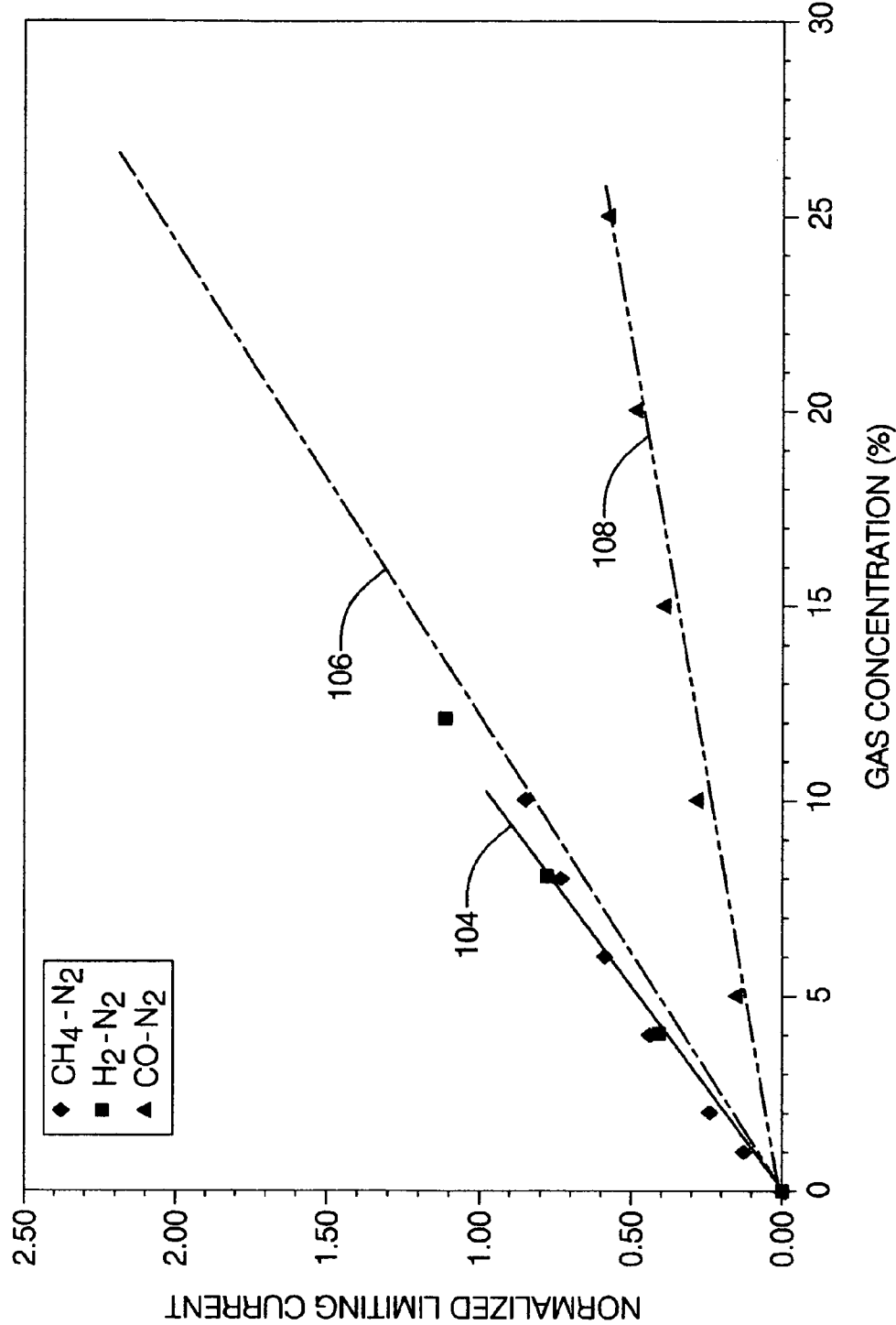
FIG. 10 is a graph illustrating normalized limiting current (y-axis) versus species concentration (x-axis) for another O/C sensor tested in three separate bi-gas systems.
Figure 11:
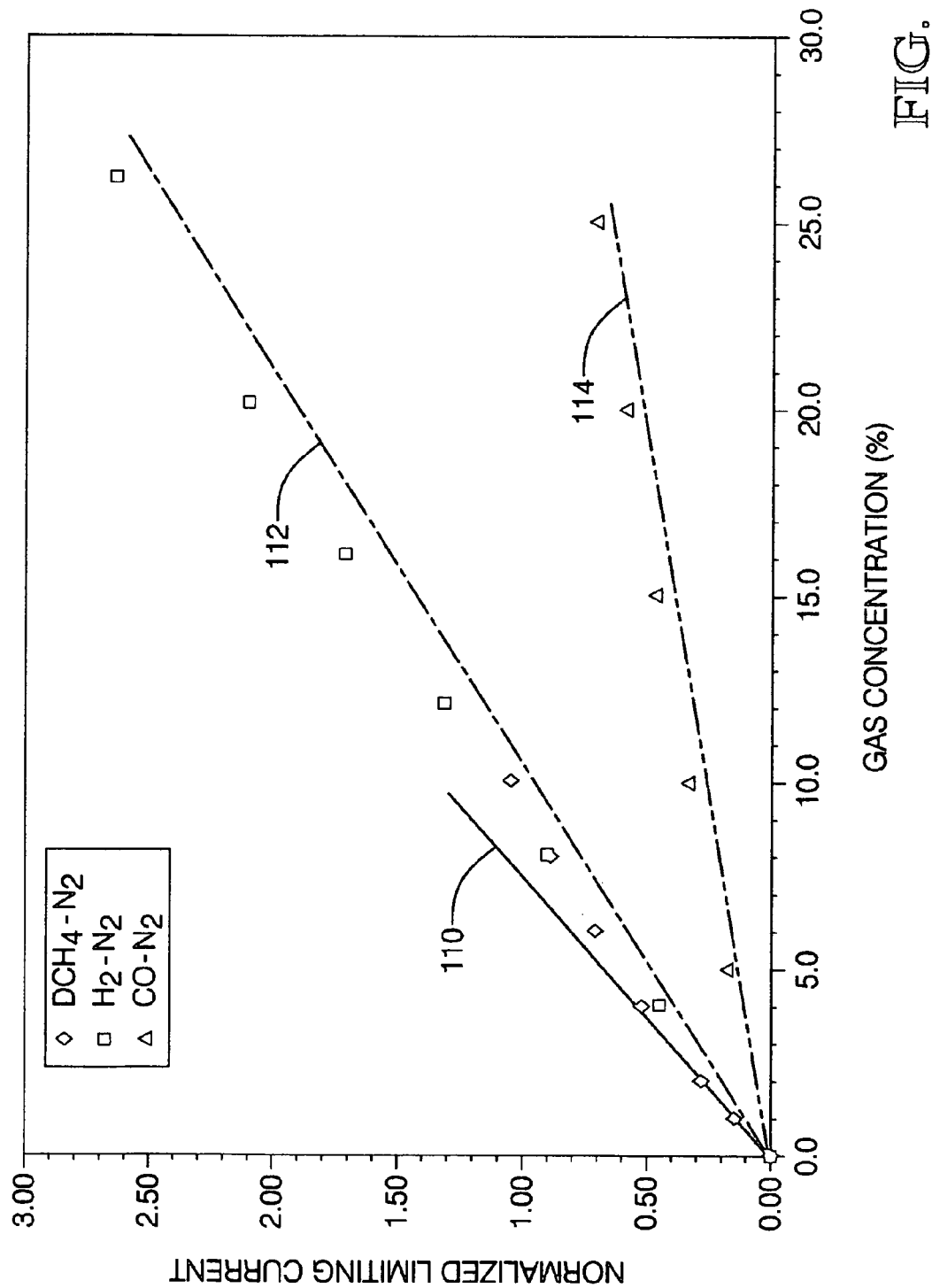
FIG. 11 is a graph illustrating normalized limiting current (y-axis) versus species concentration (x-axis) for yet another O/C sensor tested in three separate bi-gas systems.

Referring to FIGS. 9, 10, and 11, an O/C sensor of Example 1, 2, or 3 were tested in three bi-gas systems comprising $CH_4$—$N_2$, $H_2$—$N_2$ and CO—$N_2$, respectively, with the data normalized to the air limiting current (y-axis) versus gas concentrations (%, x-axis). Results shown in FIG. 9 refer to the O/C sensor of Example 1. The line 98 indicates the O/C sensor tested in a bi-gas system comprising $CH_4$—$N_2$. Line 100 indicates the O/C sensor tested in a bi-gas system comprising $H_2$—$N_2$. Line 102 indicates the O/C sensor result when tested in a bi-gas system comprising CO—$N_2$.

The O/C sensor of Example 2 was tested in three bi-gas systems comprising $CH_4$—$N_2$, $H_2$—$N_2$ and CO—$N_2$, respectively, with the data normalized to the air limiting current (y-axis) versus gas concentrations (%, x-axis), and the results are shown in FIG. 10. The line 104 indicates the O/C sensor tested in a bi-gas system comprising $CH_4$—$N_2$. Line 106 indicates the O/C sensor tested in a bi-gas system comprising $H_2$—$N_2$. Line 108 indicates the O/C sensor result when tested in a bi-gas system comprising CO—$N_2$.

The O/C sensor of Example 3 was tested in three bi-gas systems comprising $CH_4$—$N_2$, $H_2$—$N_2$ and CO—$N_2$, respectively, with the data normalized to the air limiting current (y-axis) versus gas concentrations (%, x-axis), and the results are shown in FIG. 11. The line 110 indicates the O/C sensor tested in a bi-gas system comprising $CH_4$—$N_2$. Line 112 indicates the O/C sensor tested in a bi-gas system comprising $H_2$—$N_2$. Line 114 indicates the O/C sensor result when tested in a bi-gas system comprising CO—$N_2$.

For FIGS. 9, 10, and 11 and Table 1, it can be seen that there is agreement between the data of Table 1 and the results shown in FIGS. 9, 10 and 11.

Figure 12:
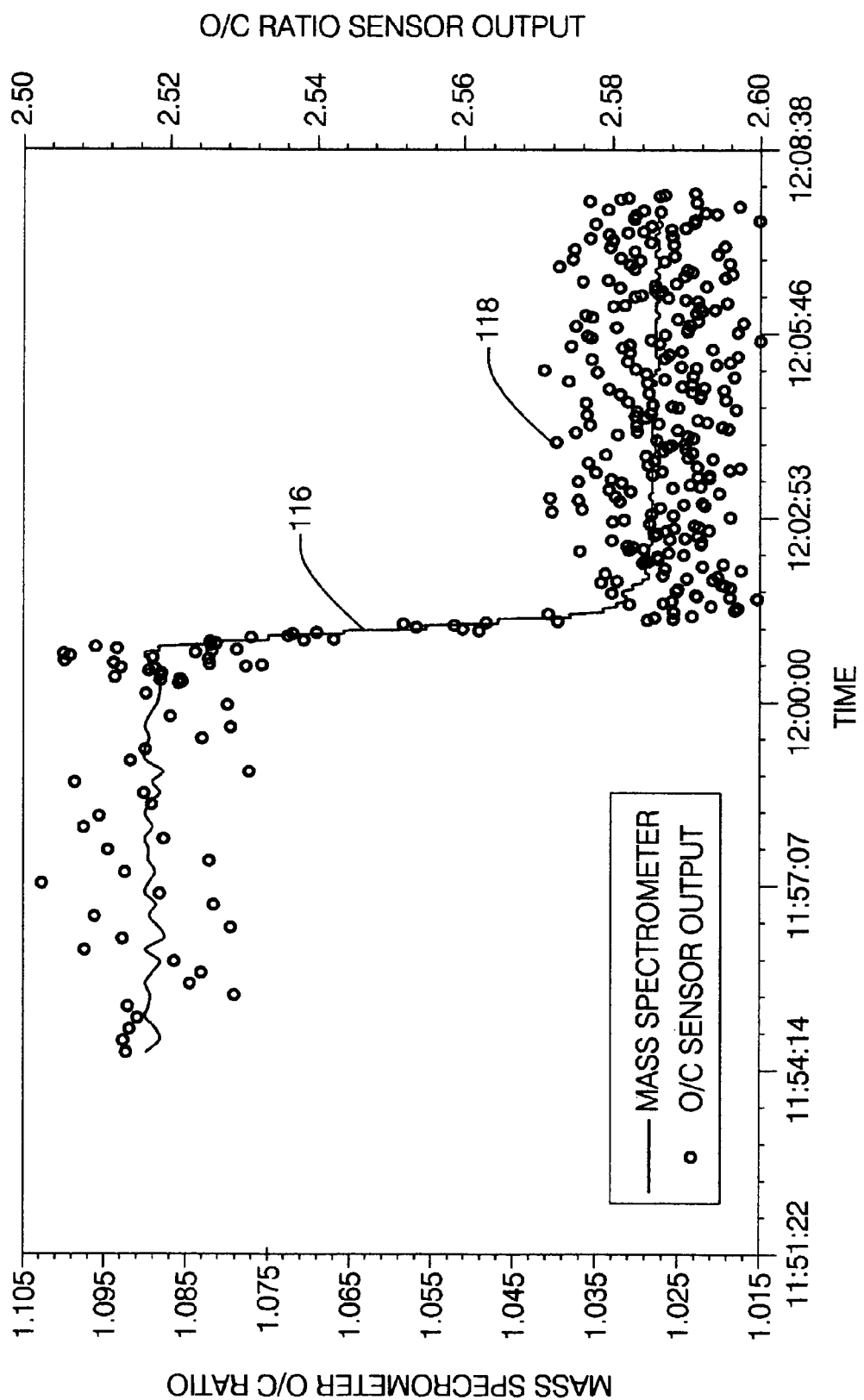
FIG. 12 is a graph illustrating reformer test results for an O/C sensor at two different O/C ratios as measured by a mass spectrometer, 1.090 and 1.025.

The O/C sensor of Example 4 was tested with a reformer running on gasoline fuel at different O/C ratios. The sensor was positioned downstream of the reformer in a post-reformer post-catalyst position. The air fuel mixture delivered to the reformer was varied. The intended O/C ratio range was between 1.15 and 1.30 and the actual O/C ratio range as determined by a mass spectrometer was between 1.029 to about 1.090. An electronic control module controlled the O/C ratio sensor with the reference emf set at 250 mV and the sensor control temperature was set at 650° C. The data was obtained by taking a reading at a rate of one reading per 1.5 seconds with a mass spectrometer. Results for this test are shown in FIG. 12. The mass spectrometer readings are indicated by line 116 and the sensor output is indicated by circles 118. The reformer was operated at two different O/C ratios, 1.088 and 1.027. As can be seen in FIG. 12, the O/C sensor tracks well the change of the O/C ratios. The sensor exhibited a noise which was determined to be ±6% of the limiting current level.

Figure 13:
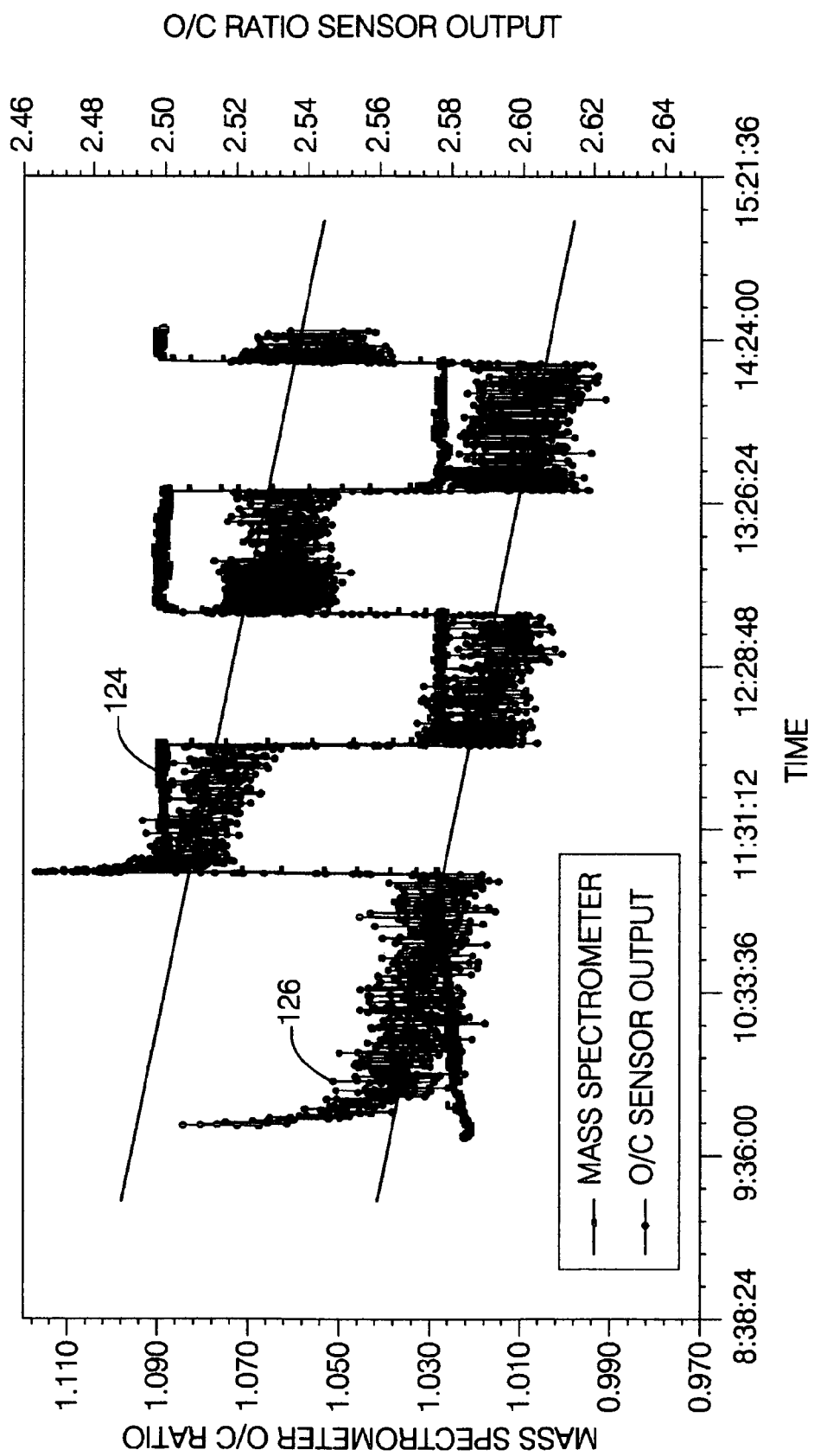
FIG. 13 is a graph illustrating reformer test results for an O/C sensor in which the reformer cycled between two O/C ratio values, 1.030 and 1.090 for about five hours.

The sensor signal is reliable showing only a slight drift over time. FIG. 13 illustrates reformer test results for the sensor of Example 4 in which the reformer cycled between two O/C ratio values, 1.030 and 1.090 for about five hours, reference numeral 124 indicating a mass spectrometer output and reference numeral 126 indicating the O/C sensor output. As shown in FIG. 13, the sensor output tracks the change of O/C ratio quite well with only a slight drift. While not wishing to be bound by theory, it is believed that sensor temperature may cause this phenomenon representing a temperature drift of about +7° C. per hour.

Figure 14:
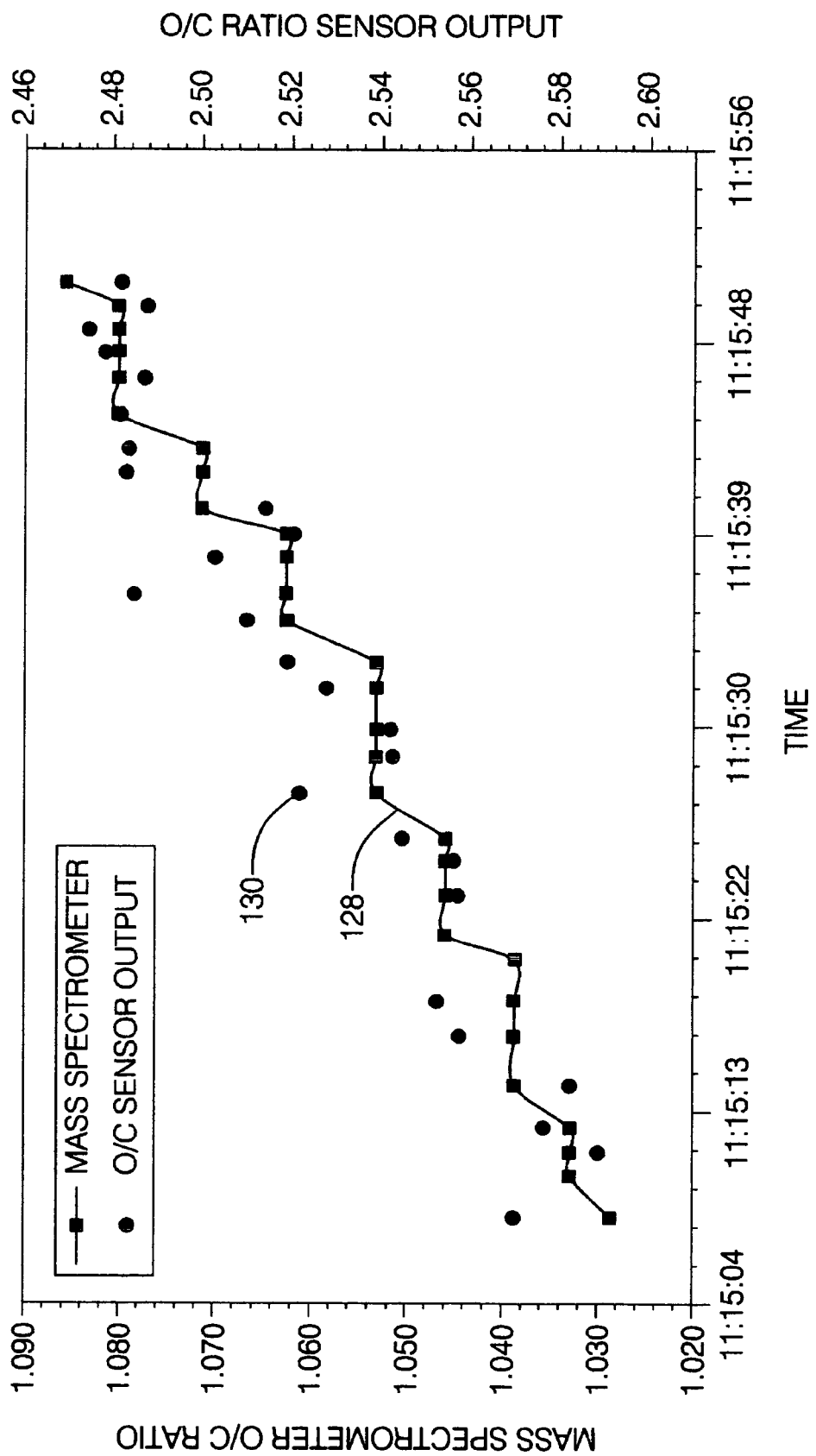
FIG. 14 is a graph illustrating the transient performance of an O/C sensor cycling from an O/C of 1.03 and an O/C of 1.09.

The transient performance of the sensor of Example 4 was tested as shown in FIG. 14 illustrating mass spectrometer O/C ratio (left y-axis) versus time (x-axis) and O/C ratio sensor output (right-y-axis) where line 128 indicates the mass spectrometer O/C ratio reading and filled circles 130 indicate the O/C sensor output. In this test, the reformer O/C ratio was stepped up from 1.030 to 1.090 in seven steps. Each step was held for about 5 to about 7 seconds. The total event took about 45 seconds. The data for both the O/C ratio sensor and mass spectrometer were taken at a rate of one point per 1.5 seconds. As can be seen in FIG. 14, although the O/C ratios (calculated from data obtained from the mass spectrometer), changed in 7 steps from 1.030 to 1.090, the O/C sensor still followed the changes of the O/C ratios, with the sensor output showing only a slight loss in resolution.

Figure 15:
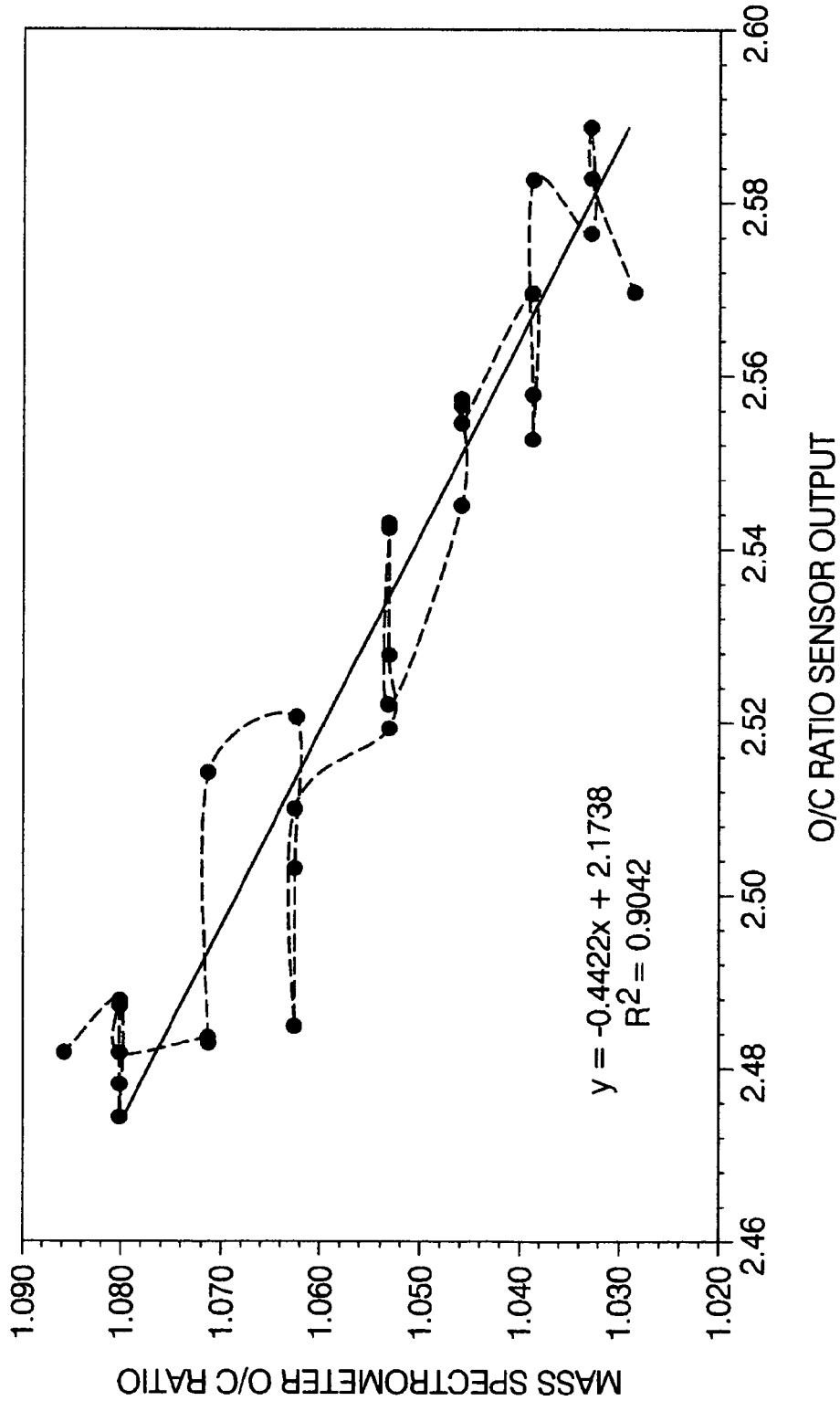
FIG. 15 is a graph illustrating a re-plotting of the data of FIG. 14.

FIG. 15 is a graph illustrating a re-plotting of the data of FIG. 14 showing mass spectrometer O/C ratio (y-axis) versus sensor output O/C ratio (x-axis).

Figure 16:
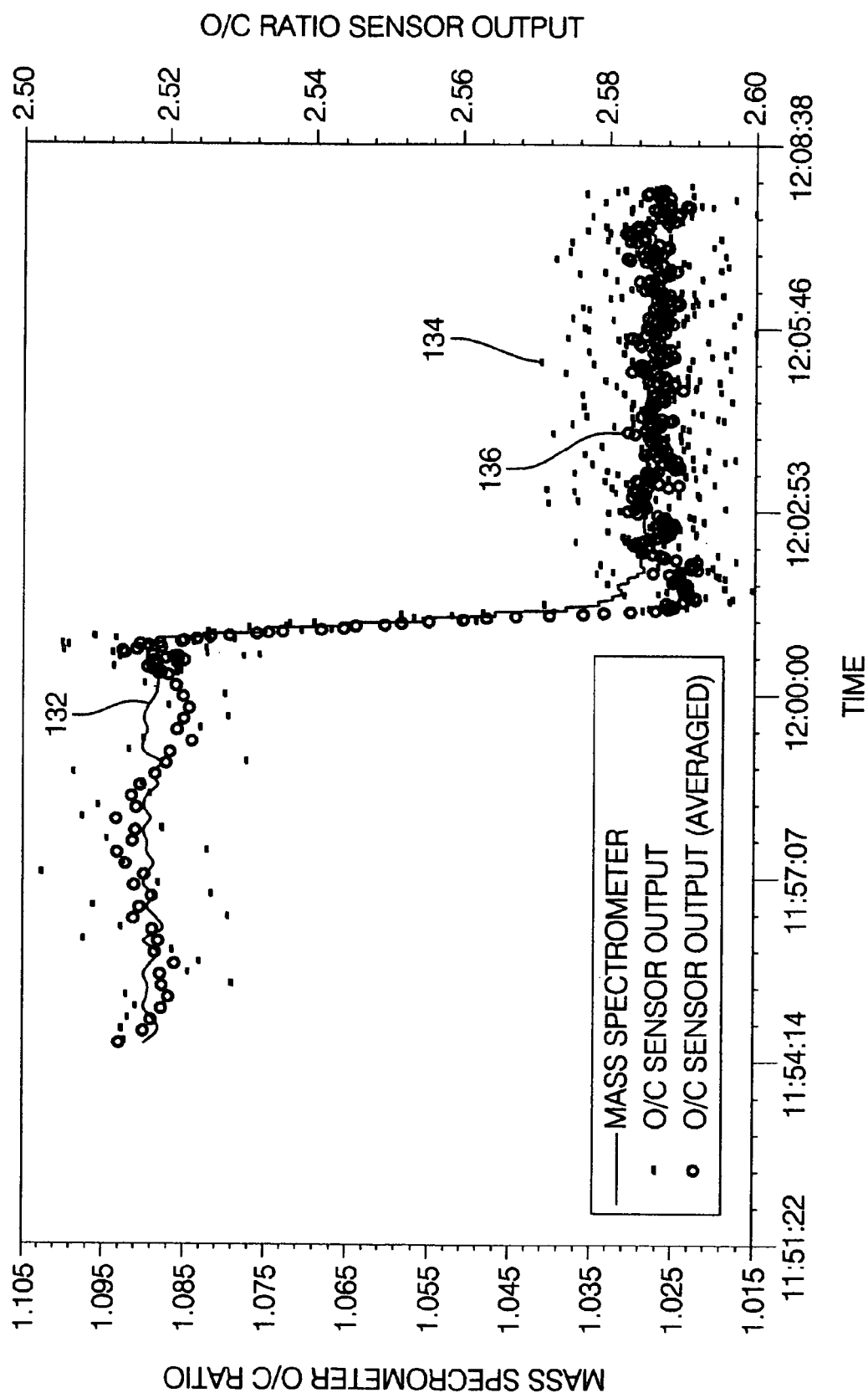
FIG. 16 is a graph illustrating a re-plotting of the data of FIG. 12 with the data being averaged prior to plotting.

Signal averaging can be employed to enhance the quality of the sensor signal output. FIG. 16 is a graph illustrating a re-plotting of the data of FIG. 12 with the data being averaged prior to plotting showing mass spectrometer O/C ratio (left y-axis) versus time (x-axis) and O/C ratio sensor output (right y-axis versus time (x-axis). Line 132 indicates mass spectrometer O/C ratio, rectangles 134 indicate O/C sensor ratio, and circles 136 indicate averaged O/C sensor output ratio.

Figure 17:
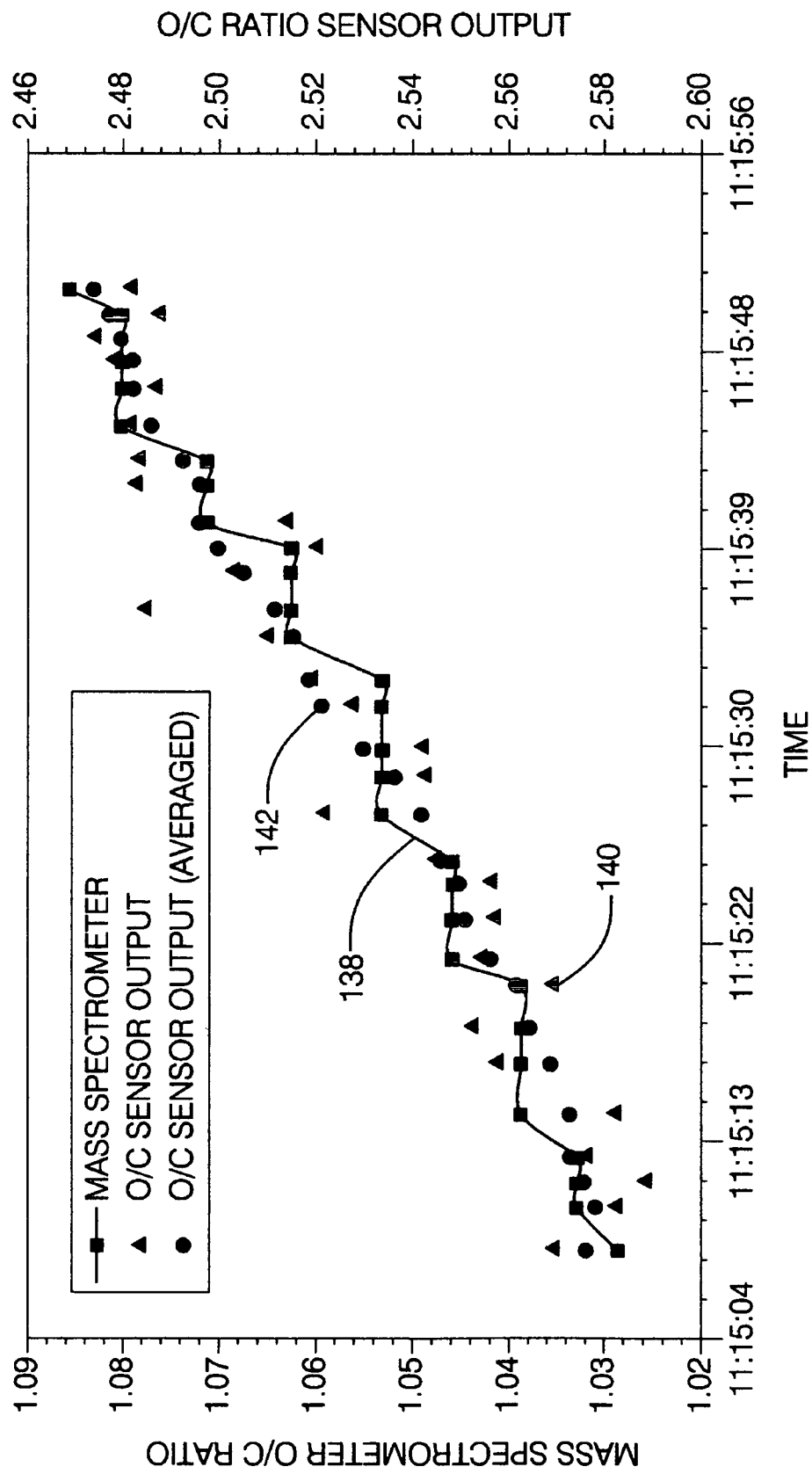
FIG. 17 is a graph illustrating a re-plotting of the data of FIG. 14 with the data being averaged prior to plotting.

FIG. 17 is a graph illustrating a re-plotting of the data of FIG. 14 with the data being averaged prior to plotting. FIG. 17 illustrates mass spectrometer O/C ratio (left y-axis) versus time (x-axis) and sensor output O/C (right y-axis) ratio sensor versus time (x-axis) with line 138 indicating mass spectrometer O/C ratio, triangles 140 indicating O/C sensor output, and circles 142 indicating averaged O/C sensor output ratio. As shown in these FIGS., an observed signal perturbation of about 1.6% enables an O/C ratio resolution of about 0.01. With signal averaging, the resolution can be improved to about ±0.005.

The sensor output peak at the stoichiometric point of O/C=1.0 (see FIG. 7) is unexpected according to FIG. 1, which shows monotonic relationships between O/C ratio and A/F ratio. However, as shown in FIGS. 5-7, the fuel vapor concentrations of the reformate drop as the O/C ratio crosses the initial stoichiometric point to the rich side. The maximum concentration of $H_2$, CO and $CH_4$ at the stoichiometric unity point indicates that the output signal would peak at the stoichiometric point. This will generate two O/C results for each given sensor output if the O/C not on its stoichiometric point. This dual result phenomenon can be alleviated by the O/C sensor having sufficient resolution and if the history of the rate of fuel delivery to the reformer becomes known to the control modulus (microprocessor). With the knowledge of the fuel delivery trend and the O/C sensor output rate, it can be determined which side of the O/C ratio data the reformate output belongs to.

The peak position and peak strength can be utilized to calibrate the effect of fuel quality (H/C) and reformer catalyst aging on O/C ratio measurement. Noting that the resolution of the sensor is dependent on the variation of H/C of the fuel unless the fuel quality is known to the control modulus, since the sensor output would peak at the stoichiometric point (O/C 1.000), which corresponds to a different A/F for each individual H/C fuel (including fuels that have oxygen-containing additives, see FIG. 1), it can be used to resolve the effect of fuel quality on the sensor resolution. In such an instance, the sensor becomes a H/C ratio sensor.

Catalyst converter can age with time and the $H_2$ concentration can decay with time. This effect applies equally to the O/C stoichiometric point. Therefore, by measuring the change of the maximum peak strength, a calibration of the catalyst aging effect on the O/C ratio measurement can also be made. In such instance, the sensor becomes a catalyst aging level sensor.

The sensors discloses herein provide a good resolution, that is <±0.0025 and fast response, that is <1.0 second. The sensors demonstrated ample resolution. Signal noise can be improved such as with hardware including electronic control circuits and/or with software such as PID (Proportional Integral Derivative) control and data averaging.

The disclosed sensors are readily prepared based on oxygen sensor multi-layer thick film technology providing a cost effective device that is easily transferred into mass manufacture.

Referring to FIG. 18, a system includes a sensing element 44 including an O/C sensor 22 positioned downstream of a fuel reformer 146 comprising, for example, a gasoline reformer, a diesel reformer, a methane reformer, a methanol reformer, or a combination thereof The O/C sensor receives a gas to be sensed, for example, reformate gas 30 which can then be fed into one or more devices 148 including, but not limited to, for example, an exhaust catalyst, an exhaust pipe, or an energy conversion device such as a fuel cell. Reformer controller 150 and sensor controller 152 and electronic circuitry (indicated generally by lines connecting controllers 150, 152 and sensing element 44) provide closed loop control of sensor temperature and maintain the sensor at a constant temperature during operation. Electronic circuitry further provides closed loop control of the sensor emf cell maintaining the emf cell at a constant emf value, for example, in the range of about 150 mV (millivolts) to about 800 mV. The pump current of the control circuit is equal to the sensor output O/C ratio.

The reformer is governed by a control module, for example, reformer controller 150, including a microprocessor to control, for example, the input air and the fuel delivery to the reformer. The sensor in combination with the reformer control module operate together comparing the direction difference between the sensor output change with the fuel delivery change to determine if the reformer as at a fuel rich side of the value O/C=1 or at a fuel lean side of the value O/C=1. In embodiments, the sensing method comprises an oxygen to carbon ratio sensing method comprising maintaining the oxygen pump current at a value equal to the output of the oxygen to carbon ratio sensor. For example, if the fuel delivery is increasing and the sensor pump current is decreasing, the O/C ratio is on the rich side. If the pump current is increasing, the O/C ratio is on the lean side. If the fuel delivery is decreasing and the sensor pump current is increasing, the O/C ratio is on the rich side. If the pump current is decreasing, the O/C ratio is on the lean side.

Calibration of the pump current to the O/C ratio is achieved, for example, by use of a look up table, or by equations in software arrangement. In embodiments, the sensor in conjunction with the reformer control module is used to determine the stoichiometric unit point of O/C by varying the fuel delivery to the reformer. The unit O/C point is the point when the maximum pump current is obtained. This searching mode can be used to calibrate the effect of different fuels, which may have different H/C ratios or having oxygen-containing additives, on the O/C ratio sensing. Further, the sensing method comprises an oxygen to carbon ratio sensing method including maintaining the oxygen pump current at a value equal to the output of the oxygen to carbon ratio sensor.

The maximum pump current value, obtained from the determination of the stoichiometric unit point described above, can be used to calibrate the effect on reformer catalyst efficiency or the effect of sensor aging on the O/C ratio sensing. Changes in catalyst efficiency may be caused, for example, by thermal aging, poisons, for example. An aged catalyst delivers less hydrogen resulting in a weaker signal output of the sensor at unit O/C ratio where the signal of the sensor is measured at maximum oxygen pump current value. Provided herein is a method to determine catalyst efficiency by determining a maximum oxygen pump current value and using the determined maximum oxygen pump current value to determine an effect on reformer catalyst efficiency. For example, the method comprises determining a stoichiometric unity point of the oxygen to carbon ratio using the sensor in conjunction with the reformer control module by varying fuel delivery to the reformer; wherein the oxygen to carbon ratio unity point is the point when a maximum oxygen pump current is obtained; and employing the determined unity point to calibrate the effect of an aging catalyst converter on the oxygen to carbon ratio sensor.

In further embodiments, the sensor in conjunction with the control module is used to calibrate the individual sensor aging effect or sensor to sensor variation effect on the O/C ratio sensing. In this operating mode, the sensor is operated in air (air is blow in when the reformer is not ignited) with the emf cell controlled at an opposite polarity of an emf value, which can have a range of about 150 mV to about 450 mV. For example, the method comprises operating the sensor in air when the reformer is not ignited; maintaining the emf cell at an opposite polarity of an emf value in a range of about 150 mV to about 450 mV or about 150 mV to about 800 mV; using the measured limiting current value in air to determine sensor aging effect or sensor to sensor variation on oxygen to carbon ratio sensing.

The sensor controller can govern the various control modes disclosed above, for example, by inputting reformer fuel delivery information into the sensor controller such as from the reformer control module.

The sensing elements comprise, in embodiments, sensors based on oxide ion conducting solid oxide electrolyte, such as, for example, yttria doped zirconia. In further embodiments, the sensing elements comprise sensors based on proton conducting solid oxide electrolyte, such as, for example, doped $SrCeO_3$, doped, for example, with 5 m (mole) % Yt, or doped $CaZrO_3$, doped, for example, with 10 m % In.

Figure 19:
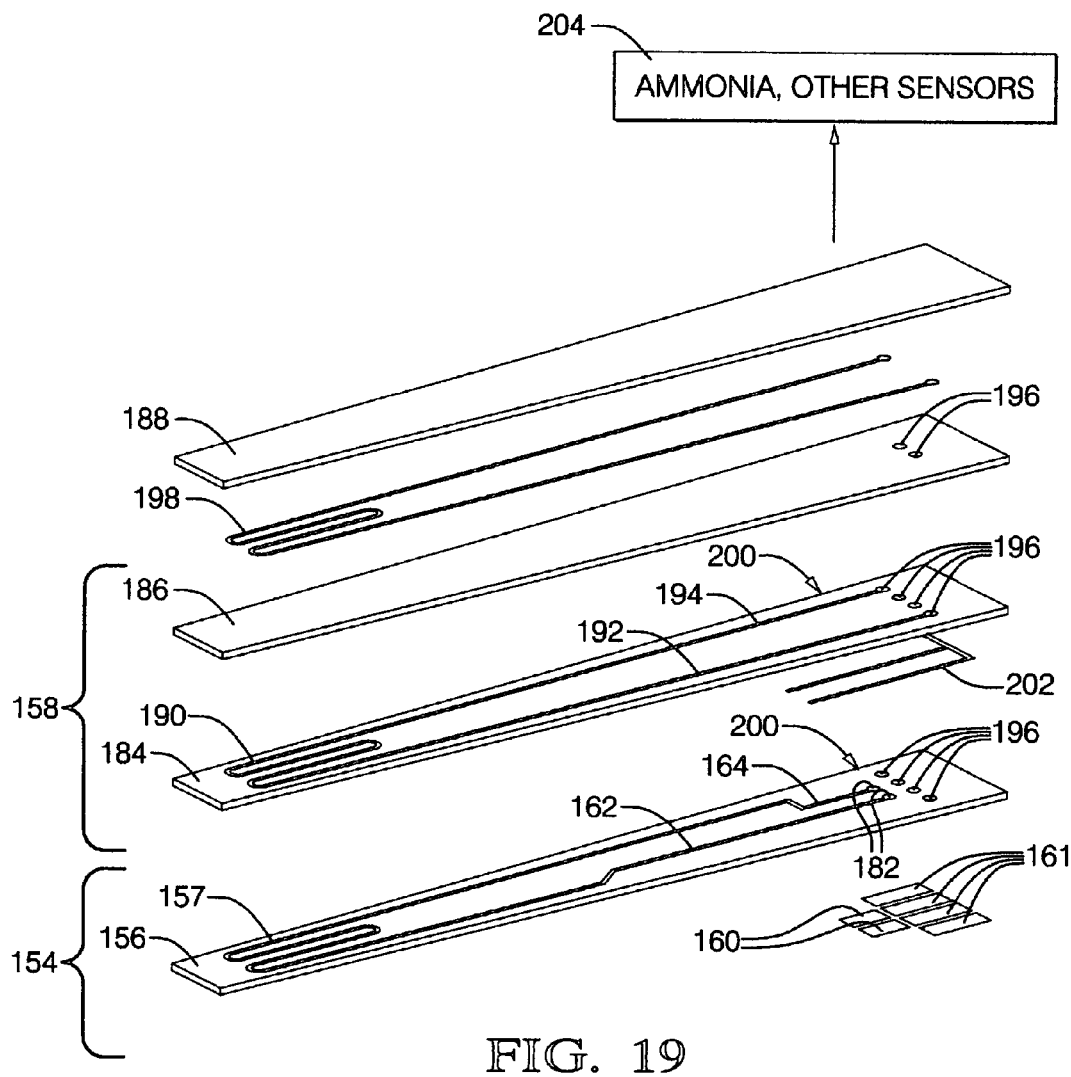
FIG. 19 is an exploded view of a portion of a sensing element including a Resistance Temperature Detector.

Referring to FIG. 19, a portion of a sensing element including a resistance temperature detector (RTD) sensor 154 and a heater 158 is provided for use in conjunction with a sensing element, such as sensing element 44 including O/C sensor 22, or other sensing elements, such as, but not limited to, an exhaust gas species sensor, an oxygen to carbon ratio sensor, a hydrogen to carbon ratio sensor, a wide range sensor, an oxygen sensor, or an ammonia sensor. RTD sensor 154 is particularly suitable for use in high temperature environments, such as exhaust gas environments, having temperatures of, for example, about 800° C. to about 1000° C. The RTD sensor 154 includes a substrate 156 comprising an insulating layer or layers. The substrate can be prepared using multi-layer thick film ceramic technology as is known in the art. Reference, for example, Published U.S. patent application Ser. No. 10/004,679, which is totally incorporated by reference herein, a continuation-in-part application of above patent application, which is totally incorporated by reference herein. The RTD substrate 156 has disposed on a side thereon high temperature RTD pads 160 and an electrode 157 including electrode leads 162 and 164 for connecting the RTD sensor 154 to RTD pads 160 through the via holes 182. However, the RTD sensors may include a plurality of leads, as necessary, for connecting to various elements depending on the application, including, but not limited to, sensing elements such as O/C sensor 22, ammonia sensors, wide range sensors, oxygen sensors, gas species sensors, such as, for example, carbon monoxide sensors, nitrogen oxide (NOx) sensors, carbon dioxide sensors, hydrocarbon sensors, etc.). In FIG. 19, heater 158 connects to the bottom heater pads 161 by way of the via holes 196 on the layers 156, 184, 186.

Heater 158 is similar to the heater 72 shown in FIG. 3. If it is desired to use a RTD for temperature sensing and control in a device such as shown in FIG. 3, RTD sensor 154 is added to the elements shown in FIG. 3. Glass 202 can be used to bond RTD 154 to the bottom portion of FIG. 3 with heater 72 in FIG. 3 comprising the heater 158 in FIG. 19, except the pad arrangement is changed. For example, the two heater pads and the two RTD pads can be arranged through via holes to connect to the RTD 154 and heater 158 and the rest of the sensor can be connected to the top pads-two pads for pumping electrodes and two pads for the emf electrodes, although not limited to this arrangement. The heater 158 includes a plurality of insulating layers, such as at least three layers, comprising a ceramic, for example, alumina layer, including insulating layers 184, 186, 188, having a heater (electrode), such as platinum electrode 190 and an electromagnetic (EM) noise filter 198, disposed between two or more insulating layers such as layers 186, 188. Heater 190 and EM noise filter 198 can be disposed by any suitable means, such as, for example, screen printing.

The heater 190 and electromagnetic (EM) noise filter 198 can be built into any part of the sensor substrate. Typically, the heater and EM noise filter are located toward one side of the substrate so that the heater current can be easily introduced without thermal loss through long via hole paths.

The RTD sensor 154 is disposed on the heater side of the substrate. The RTD electrode comprises a high temperature capable that is an electrode material suitable for use in high temperature environments found in exhaust gas sensing applications, such as about 800° C. to about 1000° C. In a particular embodiment, the RTD electrode is platinum, particularly a platinum thin film. The electrode, leads and pads can be deposited by any suitable means, including, but not limited to, screen printing, sputtering-annealing methods, laser subscription, among others. In a particular embodiment, the sputtering-annealing is employed to deposit the RTD, leads and pads. In another particular embodiment, the RTD pattern can be precision controlled by disposing using a laser subscription method.

The RTD temperature sensor 154 can comprise any suitable insulating material, particularly ceramic. In various embodiments, the substrate 12 comprises aluminum oxide ($Al_2O_3$), silicon oxide ($SiO_2$), titanium oxide ($TiO_2$), zirconium oxide ($ZrO_2$), or a combination comprising at least one of the foregoing, as well as other dielectric materials. Additionally, the substrate may comprise mixed oxides such as mullite ($3Al_2O_3$-$2SiO_2$), lanthanum aluminate ($LaAlO_3$), zirconium-aluminum oxide ($ZrO_2$—$Al_2O_3$), yttrium-zirconium-aluminum oxide ($Y_2O_3$—$ZrO_2$—$Al_2O_3$), fused silica ($SiO_2$), barium titanate ($BaTiO_3$), strontium titanate ($SrTiO_3$), aluminum-titanium oxide glass composition, cordierite-glass composition, lithium-alumina-silica ($Li_2O$—$Al_2O_3$—$SiO_2$), magnesium-aluminum-silicon oxide ($MgO$—$Al_2O_3$—$SiO_2$), sodium-aluminum-silicon ($Na_2O$—$Al_2O_3$—$SiO_2$), barium-aluminum-silicon ($BaO$—$Al_2O_3$—$SiO_2$), lithium-magnesium-aluminum-silicon ($Li_2O$—$MgO$—$Al_2O_3$—$SiO_2$), potassium-magnesium-aluminum-silicon ($K_2O$—$MgO$—$Al_2O_3$—$SiO_2$), and the like.

Layers 156 and 184 can be connected, for example via glass layer 202 shown in FIG. 19. Glass layer is applied to opposite edges of ceramic layers 156, 184, binding the layers together hermetically so as to prevent exhaust gas penetration into the RTD area which would change the values of the RID. Contact of a connecting material such as glass with the RTD, or leads, or via holes can lead to the same effect and change the RTD values eventually. Therefore glass 202 is applied only to the edge and just enough to offer a hermetic seal without touching metal parts of RTR 154.

For example, on an edge 200 of the RTD sensor 154 adjacent the heater 158 substrate surface, a high temperature glass 202 is applied to seal the edge from exposure to exhaust as. In this way, the main sensor substrate becomes the exhaust protection cover for the RTD temperature sensor 154. The function of this protective cover is to avoid exhaust gas in direct contact with the RTD. A direct contact of exhaust gas will poison the RTD by depositing impurities on RTD and changing the values of the RTD. The function of glass 202 is to offer the hermetic seal between layer 156 and layer 184.

Glass layer 202 can comprise any suitable glass layer of suitably thermal expansion coefficient as the rest of the sensor for bonding the RTD substrate to the main sensor substrate, and having a suitable soft temperature for the particular sensing application, for example, a high bond strength glass having a soft temperature greater than about 800° C., greater than about 1,000° C., or greater than about 1,200° C. In embodiments, the glass layer 202 is a glass comprising about 45 mole percent to about 70 mole percent $M^{+4}$ metal oxide, about 1 mole percent to about 25 mole percent $M^{+3}$ metal oxide, or about 10 mole percent to about 26 mole percent $M^{+3}$ rare earth oxide. For example, $M^{+4}$ metal oxides include, but are not limited to, $SiO_2$, $TiO_2$, $ZrO_2$, $HfO_2$, $GeO_2$, $SnO_2$, and $PbO_2$. Examples of $M^{+3}$ metal oxides include, but are not limited to, $Sc_2O_3$, $Y_2O_3$, $B_2O_3$, $Al_2O_3$, $Ga_2O_3$, $In_2O_3$, $Sb_2O_3$, and $Bi_2O_3$. Examples of $M^{+3}$ rare earth oxides include, but are not limited to, $La_2O_3$, $Ce_2O_3$, $Nd_2O_3$, $Sm_2O_3$, $Gd_2O_3$, $Dy_2O_3$, $Ho_2O_3$, $Er_2O_3$, $Yb_2O_3$, and $La_2O_3$.

The RTD sensor 154 can be used with other types of functional sensors, indicated generally by 204, including, for example, but not limited to, an exhaust gas species sensor, an oxygen to carbon ratio sensor, a hydrogen to carbon ratio sensor, a wide range sensor, an oxygen sensor, or an ammonia sensor.

The RTD temperature sensor can be used for precision temperature reading and precision temperature control employing an electronic controller in communication with the RTD temperature sensor and heater for reading a current or voltage signal as an indication of temperature and providing a signal to vary the supply of heater current so as to maintain the sensing element at a desired temperature. In temperature reading, a voltage source or current source is connected to the RTD through the pads and lead wires. Current or voltage drops are read as the indication of temperature. The signal is fed into a closed loop control circuit that will vary the supply of heater current to maintain the desired temperature. The linearity of the feedback, with respect to temperature, for a heater control system, provides ease of application and good control dynamics. The RTD temperature sensor provides linearity over a broad range of operation parameters.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A system for sensing the oxygen-to-carbon (O/C) ratio of a reference gas, said system comprising:
    a sensor comprising
        an oxygen pump cell having a first pump electrode and a second pump electrode disposed on opposite sides of a first solid electrolyte layer;
        the first pump electrode being directly exposed to the reference gas or indirectly exposed to the reference gas through a protective coating layer and the second pump electrode being exposed to an oxygen pump chamber including a first aperture providing a fluid connection to the reference gas;
        an emf cell having a first emf electrode and a second emf electrode disposed on opposite sides of a second solid electrolyte layer, wherein the first emf electrode comprises a material selected from the group consisting of platinum, palladium, osmium, rhodium, iridium, gold, ruthenium, and mixtures and alloys thereof, and the second emf electrode consists essentially of the same material as the first emf electrode so as to have essentially the same capability to catalyze oxygen;
        the first emf electrode sharing the same oxygen pump chamber as the second pump electrode and the second emf electrode being exposed to a reference chamber having a second aperture providing a fluid connection between the second emf electrode and the reference gas;
        wherein the reference gas comprises reformate produced by a fuel reformer fueled by an air-fuel gas mixture having an air-fuel ratio and including a reformer electronic control module;
    a sensor electronic control module in electrical communication with the sensor and further in communication with the reformer electronic control module;
    a heater disposed in thermal communication with the sensor;
    a temperature sensor disposed in thermal communication with the heater and in electronic communication with the sensor control module for maintaining the sensor at a desired operating temperature; and an electrical means in electrical communication with the sensor so as to receive a signal corresponding to the emf value at the emf cell and so as to control pump current to the oxygen pump cell to maintain a constant emf at the emf cell, and wherein a pump current value represents an equivalent to the air-fuel ratio of the air-fuel gas mixture.

2. The system of claim 1, wherein the solid electrolyte layer comprises an oxide ion conducting electrolyte or a proton conducting solid oxide electrolyte.

3. The system of claim 1, wherein the reformer comprises a gasoline reformer, a diesel reformer, a methane reformer, a methanol reformer, or a combination thereof.

4. The system of claim 1, wherein the first aperture has an opening that is sufficiently narrow such that a limiting current in air is obtained with an applied pump voltage of about 0 to about 1.5 volts.

5. The system of claim 1, wherein the second aperture has an opening sufficient to maintain the second emf electrode at chemical equilibrium with the reference gas and having a high gas diffusion rate so that the response time of the second emf electrode is not limited by the response time of the gas diffusion rate of the second aperture.

6. The system of claim 1, wherein the temperature sensor is a resistance temperature detector.

7. The system of claim 1, wherein the temperature sensor is a resistance temperature detector sensor comprising an insulating layer having a high temperature electrode disposed thereon; and a glass layer disposed between the resistance temperature detector sensor and the heater to prevent exhaust gas penetration into the resistance temperature detector.

8. The system of claim 7, wherein high temperature comprises a temperature of about 800° C. to about 1000° C.

9. The system of claim 8, wherein the high temperature electrode comprises platinum.

10. The system of claim 8, wherein the glass layer has a thermal expansion coefficient that matches a thermal expansion coefficient of the rest of the sensor.

11. The system of claim 8, wherein the glass layer comprises a glass having a softening temperature greater than about 1,000° C.

12. The system of claim 8, wherein the glass layer comprises a glass having a softening temperature greater than about 1,200° C.

13. The system of claim 8, wherein the glass layer comprises about 45 mole percent to about 70 mole percent M+4 metal oxide, about 1 mole percent to about 25 mole percent M+3 metal oxide, or about 10 mole percent to about 26 mole percent M+3 rare earth oxide.

14. The system of claim 1, wherein the first emf electrode and the second emf electrode comprise platinum.

15. The system of claim 1, wherein the electrical means includes an operational amplifier.

16. A system for sensing the oxygen-to-carbon (O/C) ratio of a reference gas, said system comprising:

a sensor comprising
an oxygen pump cell having a first pump electrode and a second pump electrode disposed on opposite sides of a first solid electrolyte layer;

the first pump electrode being directly exposed to the reference gas or indirectly exposed to the reference gas through a protective coating layer and the second pump electrode being exposed to an oxygen pump chamber including a first aperture providing a fluid connection to the reference gas, wherein the first aperture has an opening that is sufficiently narrow such that a limiting current in air is obtained with an applied pump voltage of about 0 to about 1.5 volts;

an emf cell having a first emf electrode and a second emf electrode disposed on opposite sides of a second solid electrolyte layer, wherein the first emf electrode comprises a material selected from the group consisting of platinum, palladium, osmium, rhodium, iridium, gold, ruthenium, and mixtures and alloys thereof, and the second emf electrode consists essentially of the same material as the first emf electrode so as to have essentially the same capability to catalyze oxygen;

the first emf electrode sharing the same oxygen pump chamber as the second pump electrode and the second emf electrode being exposed to a reference chamber having a second aperture providing a fluid connection between the second emf electrode and the reference gas, wherein the second aperture has an opening sufficient to maintain the second emf electrode at chemical equilibrium with the reference gas and having a high gas diffusion rate so that the response time of the second emf electrode is not limited by the response time of the gas diffusion rate of the second aperture;

wherein the reference gas comprises reformate produced by a fuel reformer fueled by an air-fuel gas mixture having an air-fuel ratio and including a reformer electronic control module;

a sensor electronic control module in electrical communication with the sensor and further in communication with the reformer electronic control module;

a heater disposed in thermal communication with the sensor;

a temperature sensor disposed in thermal communication with the heater and in electronic communication with the sensor control module for maintaining the sensor at a desired operating temperature; and an electrical means in electrical communication with the sensor so as to receive a signal corresponding to the emf value at the emf cell and so as to control pump current to the oxygen pump cell to maintain a constant emf at the emf cell, and wherein a pump current value represents an equivalent to the air-fuel ratio of the air-fuel gas mixture.

\* \* \* \* \*